(12) United States Patent
Zollars et al.

(10) Patent No.: US 10,254,164 B2
(45) Date of Patent: Apr. 9, 2019

(54) COMPACT MAPPING SPECTROMETER

(71) Applicant: NANOHMICS, INC., Austin, TX (US)

(72) Inventors: Byron G. Zollars, Georgetown, TX (US); Chris W. Mann, Austin, TX (US); Gabriel Elpers, Houston, TX (US)

(73) Assignee: NANOMMICS, INC., Austin, TX (US)

( * ) Notice: Subject to any disclaimer, the term of this patent is extended or adjusted under 35 U.S.C. 154(b) by 125 days.

(21) Appl. No.: 15/099,085

(22) Filed: Apr. 14, 2016

(65) Prior Publication Data

US 2016/0305820 A1 Oct. 20, 2016

Related U.S. Application Data

(60) Provisional application No. 62/148,266, filed on Apr. 16, 2015.

(51) Int. Cl.
| | | |
|---|---|---|
| *G01J 3/28* | (2006.01) | |
| *G01J 3/02* | (2006.01) | |
| *G01N 15/14* | (2006.01) | |
| *G01N 15/10* | (2006.01) | |

(52) U.S. Cl.
CPC ........... *G01J 3/2803* (2013.01); *G01J 3/0205* (2013.01); *G01J 3/0216* (2013.01); *G01J 3/2823* (2013.01); *G01N 15/1434* (2013.01); *G01N 15/1463* (2013.01); *G01N 2015/1006* (2013.01)

(58) Field of Classification Search
CPC ...... G01J 3/2823; G01J 3/4412; G01J 3/0205; G01J 3/2803; G01J 3/0216; G01J 3/0229
See application file for complete search history.

(56) References Cited

U.S. PATENT DOCUMENTS

| 1,176,746 A | 3/1916 | Federico |
| 2,474,061 A | 6/1949 | Moulton |
| 4,053,208 A | 10/1977 | Kato et al. |

(Continued)

FOREIGN PATENT DOCUMENTS

| WO | 2006110294 A1 | 10/2006 |
| WO | 2013116316 A1 | 8/2013 |

(Continued)

OTHER PUBLICATIONS

Kyotoku et al, Sub-Nm Resolution Cavity Enhanced Micro-Spectrometer, Optics Express, Jan. 5, 2010, pp. 102-107, vol. 18, No. 1.

(Continued)

*Primary Examiner* — Violeta A Prieto
(74) *Attorney, Agent, or Firm* — Murphy Strategic IP; George L. Murphy

(57) ABSTRACT

A compact, mapping spectrometer and various embodiments of the spectrometer are described. Methods for performing high-resolution spectroscopic, spatial, and polarimetric analyses of electromagnetic radiation across the complete electromagnetic spectrum, using spectrometer embodiments of the invention, are also described. The spectrometer and associated methods are useful for producing spectral and hyperspectral images associated with the incoming radiation and for identifying other information about electromagnetic radiation of interest.

40 Claims, 17 Drawing Sheets

(56) References Cited

U.S. PATENT DOCUMENTS

| | | | | |
|---|---|---|---|---|
| 5,225,841 | A * | 7/1993 | Krikorian | G01S 7/2813 342/204 |
| 5,264,197 | A | 11/1993 | Wang et al. | |
| 5,534,386 | A | 7/1996 | Petersen et al. | |
| 5,727,108 | A | 3/1998 | Hed | |
| 6,137,925 | A | 10/2000 | Stimple et al. | |
| 7,149,366 | B1 | 12/2006 | Sun | |
| 7,796,316 | B2 | 9/2010 | Bodkin | |
| 8,174,694 | B2 | 5/2012 | Bodkin | |
| 8,233,148 | B2 | 7/2012 | Bodkin et al. | |
| 8,433,158 | B2 | 4/2013 | Menon | |
| 8,502,974 | B2 | 8/2013 | Johnsen | |
| 8,587,849 | B2 * | 11/2013 | Gupta | H04N 1/401 348/188 |
| 8,634,014 | B2 * | 1/2014 | Kohler | H04N 1/401 348/222.1 |
| 9,250,508 | B1 * | 2/2016 | Fu | G03B 21/62 |
| 9,500,523 | B2 * | 11/2016 | Goldring | G01N 21/255 |
| 2005/0219363 | A1 * | 10/2005 | Kohler | H04N 1/401 348/187 |
| 2006/0072109 | A1 | 4/2006 | Bodkin et al. | |
| 2006/0098096 | A1 * | 5/2006 | Gupta | H04N 1/401 348/188 |
| 2009/0109518 | A1 * | 4/2009 | Atkin | G01J 3/02 359/290 |
| 2009/0188562 | A1 | 7/2009 | Pavlak | |
| 2010/0328954 | A1 | 12/2010 | Bodkin | |
| 2014/0152839 | A1 | 6/2014 | Menon | |
| 2014/0160253 | A1 | 6/2014 | Backman et al. | |
| 2014/0320858 | A1 * | 10/2014 | Goldring | G01J 3/0256 356/416 |
| 2015/0292948 | A1 * | 10/2015 | Goldring | G01N 21/255 356/326 |
| 2015/0300879 | A1 * | 10/2015 | Goldring | G01N 21/255 356/451 |
| 2015/0355024 | A1 * | 12/2015 | Goldring | G01N 21/255 356/451 |

FOREIGN PATENT DOCUMENTS

| | | | | |
|---|---|---|---|---|
| WO | | 2013188520 | A2 | 12/2013 |
| WO | | 2014053828 | A1 | 4/2014 |
| WO | WO | 2015015493 | A2 * | 2/2015 ........... G01N 21/255 |
| WO | | 2015128503 | A1 | 9/2015 |
| WO | | 2015162197 | A2 | 10/2015 |

OTHER PUBLICATIONS

Genet et al, Light in Tiny Holes, Nature, Jan. 4, 2007, pp. 39-46, vol. 445.

Redding et al, All-fiber spectrometer based on speckle pattern reconstruction, Optics Express, Mar. 11, 2013, pp. 6584-6600, vol. 21, No. 5.

Redding et al, Compact spectrometer based on a disordered photonic chip, Nature Photonics, Jul. 28, 2013, pp. 746-751, vol. 7.

Wang et al, Computational spectrometer based on a broadband diffractive optic, Optics Express, Jun. 5, 2014, pp. 14575-14587, vol. 22, No. 12.

Riboli et al, Engineering of light confinement in strongly scattering disordered media, Nature Materials, May 18, 2014 Online, pp. 720-725, vol. 13.

Zhu et al, Internal Reflection of Diffusive Light in Random Media, Physical Review A, Sep. 15, 1991, pp. 3948-3959, vol. 44, No. 6.

Redding et al, Using a multimode fiber as a high resolution, low loss spectrometer, Optics Letters, Aug. 15, 2012, pp. 3384-3386, vol. 37, No. 16.

Momeni et al, Integrated photonic crystal spectrometers for sensing applications, Optics Communications, Aug. 1, 2009, pp. 3168-3171, vol. 282, No. 15.

Redding et al, Noise analysis of spectrometers based on speckle pattern reconstruction, Applied Optics, Jan. 20, 2014, pp. 410-417, vol. 53, No. 3.

Conley et al, Light Transport and Localization in Two-Dimensional Correlated Disorder, Physical Review Letters, Apr. 7, 2014, pp. 143901-1-143901-5, vol. 112, No. 14.

Mazilu et al, Random super-prism wavelength meter, Optics Letters, Dec. 20, 2013, pp. 96-99, vol. 39, No. 1.

Pollanen et al, Globally anisotropic high porosity silica aerogels, Journal of Non-Crystalline Solids, Jul. 9, 2008 Online, pp. 4668-4674, vol. 354, No. 40-41.

Bromberg et al, Generating Non-Rayleigh Speckles with Tailored Intensity Statistics, Physical Review Letters, May 29, 2014, pp. 213904-1-213904-5, vol. 112, No. 21.

Cooksey et al, Reflectance measurements of human skin from the ultraviolet to the shortwave infrared (250 nm to 2500 nm), Proc. SPIE, May 23, 2013, pp. 87340N1-87340N9, vol. 8734.

Cooksey et al, A collection and statistical analysis of skin reflectance signatures for inherent variability over the 250 nm to 2500 nm spectral range, Proc. SPIE, Jun. 4, 2014, pp. 908206-1-908206-11, vol. 9082.

Duparre et al, Relation between light scattering and the microstructure of optical thin films, Applied Optics, Oct. 1, 1993, pp. 5475-5480, vol. 32 No. 28.

Sayre et al, Design and characterization of 90 GHz feedhorn-coupled TES polarimeter pixels in the SPTpol camera, Proc. SPIE, Oct. 5, 2012, pp. 845239-1-845239-12, vol. 8452.

Moss et al, Finite-Difference Time-Domain Simulation of Scattering From Objects in Continuous Random Media, IEEE Transactions on Geoscience and Remote Sensing, Jan. 1, 2002, pp. 178-186, vol. 40, No. 1.

Robbie et al, Fabrication of thin films with highly porous microstructures, Journal of Vacuum Science and Technology A, May 1995, pp. 1032-1035, vol. 13, No. 3.

Hsu et al, The Formation of Uniform Colloidal Particles of Magnesium Fluoride and Sodium Magnesium Fluoride, , Journal of Colloid and Interface Science, Jul. 15, 1996, pp. 142-148, vol. 181, No. 1.

Raz et al, Sequential filtering for color image acquisition, Optics Express, Oct. 22, 2014, pp. 26878-26883, vol. 22, No. 22.

Headwall Photonics, Hyperspec® Snapshot Sensor Commercializes Handheld Hyperspectral, Headwall Photonics Press Release, Mar. 20, 2014, www.headwallphotonics.com/press-releases/press-releases-blog/bid/339855/Hyperspec-SNAPSHOT-Sensor-Commercializes-Handheld-Hyperspectral.

Nandiyanto et al, Nanometer to Submicrometer Magnesium Fluoride Particles with Controllable Morphology, Langmuir, Jun. 17, 2010, pp. 12260-12266, vol. 26, No. 14.

Shi et al, An Investigation Into the Sintering of Magnesium Fluoride Optical Material by Microwave, Journal of Minerals & Materials Characterization & Engineering, 2004, pp. 105-108, vol. 3, No. 2.

Tack et al, A Compact, High-speed and Low-cost Hyperspectral Imager, Proc. SPIE, Feb. 9, 2012, pp. 82660Q-1-82660Q-13, vol. 8266, Silicon Photonics VII.

Vacassy et al, Synthesis of Controlled Spherical Zinc Sulfide Particles by Precipitation from Homogeneous Solutions, Journal of the American Ceramic Society, Oct, 1998, pp. 2699-2705, vol. 81, No. 10.

Marinel et al, Broadband dielectriccharacterizationofTiO2 ceramics sintered through microwave and conventional processes, Ceramics International, Jun. 15, 2012, pp. 299-306, vol. 39 (2013).

Oh et al, UV-Assisted Chemical Sintering of Inkjet-Printed TiO2 Photoelectrodes for Low-Temperature Flexible Dye-Sensitized Solar Cells, Journal of the Electrochemical Society, Aug. 29, 2012, pp. H777-H781, vol. 159, No. 10.

Duan et al, Characterization of ZnSe microspheres synthesized under different hydrothermal conditions, Transactions of Nonferrous Metals Society of China, 2014, pp. 2588-2597, vol. 24 (2014).

Harris, Development of hot-pressed and chemical-vapor-deposited zinc sulfide and zinc selenide in the United States for optical windows, Proc. SPIE, Window and Dome Technologies and Materials X, 2007, pp. 654502-1-654502-27, vol. 6545.

Fujihara et al, Role of Organic Additives in the Sol-Gel Synthesis of Porous CaF2 Anti-Reflective Coatings, Journal of Sol-Gel Science and Technology, Jun. 2002, pp. 147-154, vol. 24, No. 2.

(56) References Cited

OTHER PUBLICATIONS

Kim et al, Sintering behaviour of monodispersed ZnS powders, Journal of Materials Science, Oct. 1997, pp. 5101-5106, vol. 32, No. 19.

Henke et al, X-Ray interactions: photoabsorption, scattering, transmission, and reflection, at E=50-30,000 eV, Z=1-92, Atomic Data and Nuclear Data Tables, Jul. 1993, pp. 181-342, vol. 54, No. 2.

Genack et al, Relationship between Optical Intensity, Fluctuations and Pulse Propagation in Random Media, Europhysics Letters, Feb. 15, 1990, pp. 331-336, vol. 11, No. 4.

Bott et al, Electromagnetic energy within dielectric spheres, Journal of the Optical Society of America A, Aug. 1987, pp. 1361-1365, vol. 4, No. 8.

\* cited by examiner

| Spectral Band | Wavelength Range | Scatterer in Media | Index Contrast (m) | Example Detector | Fill Fraction ($\varphi$) | Scatterer Radius (nm) | Scatter Layer Thickness (L) $\mu m$ | Calculated Average Spectral Resolving Power ($\lambda/d\lambda$) | Average Transmission ($\tau$) |
|---|---|---|---|---|---|---|---|---|---|
| UV | 150 - 400 nm | sintered MgF$_2$ in air | 1.4 | δ-doped back-thinned CCD | 0.3 | 300 | 7.48 | 130 | 38% |
| VIS | 400 - 800 nm | TiO$_2$ in PMMA | 1.73 | Silicon CCD or CMOS | 0.15 | 200 | 6.77 | 110 | 27% |
| SWIR | 900 - 1,800 nm | sintered SiO$_2$ in air | 1.4 | InGaAs SWIR FPA | 0.3 | 1,650 | 37 | 110 | 42% |
| MWIR | 3 - 5 $\mu m$ | Sintered ZnS in air | 2.2 | HgCdTe FPA | 0.3 | 1,910 | 31 | 120 | 21% |
| LWIR | 8 - 15 $\mu m$ | Sintered ZnS in air | 2.2 | Microbolometer array, e.g., amorphous silicon | 0.3 | 3,580 | 54.4 | 90 | 19% |

FIG. 8

COMPACT MAPPING SPECTROMETER

This application claims priority under 35 U.S.C. § 119 to U.S. Provisional Application No. 62/148,266 filed Apr. 16, 2015, which is incorporated by reference herein in its entirety.

STATEMENT REGARDING FEDERALLY FUNDED RESEARCH

This invention was made with government support under NASA contract NNX14CG54P. The government has certain rights in the invention.

FIELD OF THE INVENTION

This invention is related to mapping spectrometers and methods for their use in separating, identifying, and imaging spectral and polarization components of radiation.

Spectral detectors gather electromagnetic radiation from a scene and separate the radiation into individual wavelengths or narrow spectral bands. A detector then detects and measures the spectrally-separated radiation and converts the resulting information to electrical signals that represent the spectral composition of the radiation. Mapping spectrometers, including multispectral and hyperspectral imagers, associate these spectra with a position on a spatial or angular map. Multispectral and hyperspectral detection and imaging have applications in a broad array of fields such as satellite surveillance, planetary science, medicine, and environmental monitoring. Hyperspectral detectors and associated methods of analysis are also useful for tracking and detecting chemical or physical markers. In manufacturing, spectral imaging is employed for quality assurance purposes, for example, the verification that spectral markers in a product or component meet specific parameters. Hyperspectral detectors may also be sensitive to the polarization of the input light, and a measured spectro-polarimetric image can contain additional information about metallic objects or aerosol size distributions in a scene.

Most current hyperspectral imaging systems require numerous optical components, complex spectroscopic instrumentation, and precision alignment, and are large and expensive. In addition, most hyperspectral imaging systems utilize spatial scanning, i.e., scanning wide, thin swaths of a scene in a single image frame, which requires motion such as the rastering of a mirror or movement of an airplane or satellite across a region of landscape or a planet for capturing the image swaths. An entire image or scene can be assembled and processed only after all the swaths have been captured. "Snapshot" hyperspectral detectors that capture the spectral components in an entire image with a single exposure are commercially available (Headwall Photonics Inc., Fitsburg Mass., 01420; HYPERSPEC® SNAPSHOT), but these are not chip-scale and require bulky and expensive hardware to achieve meaningful spectral identification. A chip-scale, multispectral-mosaic imager (imec; Kapeldreef 75, 3001 Leuven, Belgium) and an etalon-based hyperspectral imager have been described (Raz and Mendlovic, Optics Express (2014) 22(22):26878-26883], but are complex, have limited spectral band resolution, reject all out-of-band radiation leading to low radiometric efficiency, can inadvertently pass higher-order light, introduce spatial-spectral artifacts, and/or have angular acceptance issues.

Improvements to spectrometers for hyperspectral imaging have focused on optical components (e.g., lenses, diffraction gratings, filters) and other hardware. Improvements in methods for separating electromagnetic radiation for non-arrayed spectroscopy systems, such as the use of speckling from multimode fibers, have increased the ability to capture high quality spectroscopic information, but these techniques require many meters of fiber and are unsuited for chip-scale integration (Redding et al., Applied Optics (2014) 52:410-417; Mazilu et al., Optics Letters (2014) 39:96-99; Redding & Cao, Optics Letters (2012) 37:3384-3386). Furthermore, the existing approaches to hyperspectral imaging require extensive supporting hardware.

SUMMARY

Described herein are a compact, mapping spectrometer and associated embodiments and methods of performing high-resolution spectroscopic and polarimetric analyses and imaging of incoming electromagnetic radiation across broad regions of the electromagnetic spectrum. Desirable characteristics of the mapping spectrometer described herein include high radiometric efficiency, high spectral resolution, large angular acceptance of incident radiation, spatial registration of spectral components, absence of moving parts, and chip-scale packaging dimensions.

Embodiments of the mapping spectrometer utilize disordered media (scatterers) and detector arrays to separate and identify the spectral and polarization components of electromagnetic radiation incident on a radiation scatter layer. The spectrometer and associated methods of the invention simultaneously overcome multiple challenges associated with the use of disordered media including, (1) the need for electromagnetic radiation entering the media to have coherence, which is not the case in any arbitrary real scene, (2) sufficiently separating (scattering) the electromagnetic radiation into spectral components with intensities sufficient for identification by a detector, (3) coupling the electromagnetic radiation into the spectrometer without the use of mechanical scanning or bulky optical components that defeat the advantages of using thin layers of disordered scattering media, and (4) compatibility of the mapping spectrometer with a sufficiently small package, such as for example chip-scale packaging, such that multiple spectrometers can be arrayed together in a compact form factor.

The mapping spectrometer and associated embodiments, including for example, methods for separating and identifying spectral components of electromagnetic radiation and constructing hyperspectral images, overcome other problems and shortcomings of current hyperspectral systems. Spectrometer embodiments of the invention are capable of capturing an entire hyperspectral cube (a data set representing two spatial or angular dimensions, plus a third spectral dimension) in a single frame, without scanning. The physics applicable to embodiments of the invention is not limited to a specific band of electromagnetic radiation. As such, embodiments of the spectrometer may operate, detect, and image electromagnetic radiation in any spectral band, ranging from soft X-rays to the microwave band. Additional embodiments of the spectrometer are capable of identifying and analyzing radiation from numerous spectral bands simultaneously. Various aspects and embodiments of the invention have numerous applications including, by way of example only, uses in satellite imaging for identification of remote objects, in tracking and detecting chemical and physical markers in a variety of settings, in manufacturing quality control systems, and in medical imaging.

In one embodiment of the invention, the mapping spectrometer comprises (1) an array of apertures configured to allow for passage of electromagnetic radiation through the apertures, (2) a detector array, and (3) a scatter layer positioned between the aperture array and the detector array and positioned to receive electromagnetic radiation passing through the aperture array and to direct at least one spectral component of the electromagnetic radiation to the detector array for detection. In embodiments of the invention, the array of apertures is positioned to allow for passage of electromagnetic radiation arriving at the aperture array through the apertures to the scatter layer. In embodiments of the invention, the scatter layer is positioned to receive electromagnetic radiation passing through the aperture array and to scatter at least one spectral component of the electromagnetic radiation to the detector array. The scatter layer separates one or more of the spectral components of radiation passing through the aperture array. Different wavelengths and/or polarizations of radiation are scattered differently upon interaction with the scatter layer and illuminate a specific and reproducible set of pixels on the detector array, producing a distinct speckle pattern for each wavelength on the detector array. Because the intensities of speckle patterns of different wavelengths and/or polarizations combine linearly at the detector, each speckle pattern serves as a basis vector representing the intensity of the corresponding wavelength present in the incident light. After calibration of the spectrometer, which comprises measuring the speckle pattern associated with one or more selected wavelengths of radiation, an unknown spectrum of radiation passing through the aperture array can be computationally reconstructed using the set of basis vectors.

In embodiments of the invention, an array of apertures may comprise apertures having diameters that are substantially equal and may comprise apertures having diameters that differ among the apertures. In some embodiments of the invention, an array of apertures comprises apertures having diameters that are from about one-tenth times the length of the shortest wavelength of the at least one spectral component to be detected to about one hundred times the length of the longest wavelength of the at least one spectral component to be detected. In additional embodiments of the invention, an array of apertures comprises apertures having diameters that are from about one-tenth times the length of the shortest wavelength of the at least one spectral component to be detected to about ten times the length of the longest wavelength of the at least one spectral component to be detected. In still further embodiments of the invention, an array of apertures comprises apertures having diameters that are from about one-half times the length of the shortest wavelength of the at least one spectral component to be detected to about to two times the length of the longest wavelength of the at least one spectral component to be detected. It is anticipated that any combination of apertures of various diameters may be useful in aspects of the invention. In some embodiments of the invention apertures in an aperture array are arranged in a periodic pattern. An array of apertures may be a one-dimensional (1D) array or a two-dimensional (2D) array.

In some embodiments of the invention, the aperture array comprises a first surface or side and an opposing second surface or side. In various aspects of the invention, the aperture array may comprise a reflective coating on the surface, facing the scatter layer. In further spectrometer embodiments, an aperture array may comprise a non-transparent layer having perforations. In some aspects of the invention, the non-transparent layer may comprise a film that absorbs electromagnetic radiation or may comprise a metal. In some further embodiments, an aperture array further comprises an aperture array support. In certain aspects of the invention, the array support may be transparent to electromagnetic radiation and may comprise one or more than one transparent polymer, ceramic, glass, and/or crystal. In other embodiments of the invention, the scatter layer may abut the aperture array and may provide support for the aperture array. In other embodiments, a gap is present between the scatter layer and the aperture array and/or between the scatter layer and the detector array.

Some embodiments of the mapping spectrometer of the invention further comprise an array of concentrators configured to gather and concentrate electromagnetic radiation prior to passage of the electromagnetic radiation through the apertures. In some aspects of the invention, a concentrator array may comprise one concentrator. In other aspects of the invention a concentrator array comprises a plurality of concentrators. If present, a concentrator array is positioned to gather, concentrate, and direct radiation to the array of apertures, thereby increasing the intensity of radiation at the apertures, resulting in higher radiometric efficiency of the spectrometer. In embodiments of the invention having a concentrator array, a single concentrator concentrates radiation to a single aperture of the aperture array. In some embodiments, concentrators have integrated apertures. Concentrators may comprise any of a variety of structures and shapes. Some exemplary concentrators and materials useful in embodiments of the invention include compound parabolic concentrators, lenses, etched Si wafers, machined metal feedhorns, and tapered transparent media that include fiber plate arrays (e.g., fiber optic tapers and fiber optic faceplates). In some aspects of the invention, concentrators have metallic or dielectric coatings on their external surfaces. In other aspects of the invention, concentrators have a reflective inner surface. Concentrators having elliptical, rectangular, square, or circular cross sections or any combinations of these may be useful in a variety of spectrometer embodiments.

In some aspects of the invention concentrators are "open structures", such that incoming radiation enters an open end of a light-gathering concentrator. Concentrators that are open structures typically comprise an open end that is distal to the aperture array and another end that is proximal to the aperture array. However, it is not a requirement that concentrators useful in embodiments of the invention be "open" structures.

Embodiments of the mapping spectrometer may have modifications to various spectrometer components and various arrangements of spectrometer components that are useful in different applications. By way of example only, various spectrometer components may have a reflective and/or anti-reflective coating on one or more surfaces, including aperture arrays, scatter layers, concentrators, and scene element isolators.

Scatter layers useful in embodiments of the invention may take any of numerous forms, may be manufactured by a variety of methods from any of numerous materials or combination of materials, and may comprise various modifications including for example reflective and/or anti-reflective surfaces and surface relief structures on one or more surfaces. In some embodiments of the invention, a scatter layer comprises a first surface also referred to as a first "side" facing the second surface of the aperture array and a second opposing surface or side facing the detector array. In other aspects of the invention a scatter layer may comprise other surfaces. Additionally, the thickness of the scatter layer may vary among embodiments of mapping spectrometers of the invention. In some embodiments of the invention a scatter layer may have a thickness of about 1 nm to about 1 cm inclusive. In some aspects of the invention the distance between the aperture array and the detector array is from about 1 nm to about 1 cm inclusive. In further embodiments of the invention, a scatter layer may be discontinuous, that is the scatter layer is not present as a continuous layer extending entirely across a detector array.

In some embodiments of the invention, a scatter layer may comprise transparent or translucent media, such as for example, one or more than one polymer, ceramic, glass, and/or crystal. Some transparent polymers that are useful as media in scatter layers include for example, acrylics—including PMMA, polyamides—including nylon, polyvinyls, polycarbonates, polystyrenes, silanes, silicones, polydimethylsiloxane polypropylenes, polyimides, polymethylpentene, fluropolymers, polyesters, optical epoxies, and stilbene. In certain specific embodiments, the transparent polymer medium comprises one or more than one of PMMA, polystyrenes, fluoropolymers, polycarbonates, silicones, polymethylpentene, polyesters, optical epoxies, and polydimethylsiloxane. Transparent media may also comprise voids or structural inhomogeneities. In some embodiments the refractive index of the transparent medium is inhomogeneous.

In some aspects of the invention a scatter layer comprises scatterers that are particles. Particles may be any of a variety of materials that are useful for scattering spectral components of radiation. Some exemplary particle scatterers include metal, ceramic, and polymer particles. In some embodiments, particle scatterers are present in a medium. In other embodiments, particle scatterers are not associated with or present in a medium.

In additional embodiments of the invention a scatter layer may comprise a metal film which may comprise one or more than one of Al, Ag, Au, B, Be, Co, Cu, Fe, Mg, Mo, Nb, Ni, Pb, Pd, Pt, Rh, Ta, Ti, V, Zn, and Zr. In some embodiments of the invention, the metal film has a thickness from about 5 nm to about 5,000 nm. In some embodiments, the metal film may have a thickness from about 20 nm to about 200 nm.

Scatterers may be present as agglomerations without a medium or be suspended in a transparent or translucent medium. Scatter layers with transparent media may further comprise an agglomeration of, for example, metal, ceramic or polymer scatterer particles. In some specific embodiments, a transparent scatter layer medium may comprise an agglomeration of one or more than one ceramic scatterer particle, such as for example, $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, CdTe, ZnS, ZnSe, diamond, Si, Ge, $Ba(NO_3)_2$, BBO, KDP, $LiNbO_3$, ZGP, LiF, CsI, NaCl, KBr, AlN, $Si_3N_4$ and SiC, which may be suspended in the transparent scatter layer medium. In some aspects of the invention, the transparent medium comprises one or more than one polymer such as acrylics, PMMA, polyamides, nylon, polyvinyls, polycarbonates, polystyrenes, silanes, polydimethylsiloxane, polypropylenes, polyimides, polymethylpentene, fluoropolymers, polyesters, optical epoxies, and stilbene. In other aspects of the invention the transparent medium comprises one or more than one ceramic, glass, or crystal. In some aspects of the invention the one or more than one ceramic, glass, or crystal are selected from the group consisting of $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, CdTe, ZnS, ZnSe, diamond, Si, Ge, $Ba(NO_3)_2$, BBO, KDP, $LiNbO_3$, ZGP, LiF, CsI, NaCl, KBr, AlN, $Si_3N_4$ and SiC.

In other embodiments of the invention, a scatter layer may comprise scatterer particles that are agglomerations comprising one or more than one of acrylics, PMMA, polyamides, nylon, polyvinyls, polycarbonates, polystyrenes, silanes, polydimethylsiloxane, polypropylenes, polyimides, polymethylpentene, fluoropolymers, polyesters, optical epoxies, and stilbene, which may or may not be suspended in a transparent scatter layer medium. In one aspect of these embodiments, a transparent medium comprises one or more than one polymer such as acrylics, PMMA, polyamides, nylon, polyvinyls, polycarbonates, silicones, polystyrenes, silanes, polydimethylsiloxane, polypropylenes, polyimides, polymethylpentene, fluoropolymers, polyesters, optical epoxies, and stilbene.

Detector arrays for use in embodiments of the spectrometer may also vary in specific aspects of the invention and may comprise one or more than one CCD array, CMOS array, back-thinned CCD array, focal plane array including InGaAs, InSb, PtSi, CdTe, PbSe, and HgCdTe focal plane arrays, microbolometer array, silicon array, organic photodetector array, Golay cell array, rectenna array, and antenna arrays. In some embodiments of the invention, one or more detector arrays have a wavelength-converting coating. Detector arrays useful in embodiments of the invention may comprise pixel arrays having a variety of shapes, sizes, and dimensions. In some embodiments, the array of pixels on a detector is at least a 2×2 array. In other embodiments, the array of pixels on a detector comprises between 5 pixels and $10^{12}$ pixels.

In some embodiments of the invention, spectrometers may comprise scene element isolators to restrict scattered components of radiation to specific groups of detector pixels. In some aspects of the invention, scene element isolators have reflective surfaces. In some exemplary spectrometer embodiments, at least one scene element isolator comprises an etched Si wafer. Scene element isolators having other compositions are also contemplated. In some aspects of the invention, scene element isolators may be present within a scatter layer and may surround selected regions of a scatter layer. In other aspects of the invention scene element isolators may scatter spectral components of radiation, thereby functioning as a scatter layer.

In further embodiments of the invention, a spectrometer comprises imaging optics. Imaging optics may comprise one or more than one of an objective, a photographic lens, a periscope, field-flattening optics, telecentric optics, pericentric optics, a telescope, and a microscope. In some embodiments, imaging optics are positioned to form an image of a scene at the plane of the mapping spectrometer.

Some embodiments of a spectrometer of the invention further comprise a polarization filter configured to select for polarized electromagnetic radiation prior to passage of the electromagnetic radiation through the array of apertures or a depolarization filter configured to randomize the polarization of electromagnetic radiation prior to passage of the electromagnetic radiation through the array of apertures.

In one exemplary spectrometer embodiment, the at least one spectral component has a wavelength from 1 nm to 200 nm, array apertures have diameters from about 5 nm to about 800 nm, the scatter layer has a thickness from about 3 μm to about 30 μm and comprises an agglomeration of metal particles having diameters from about 1 nm to about 400 nm.

In some exemplary spectrometer embodiments, the at least one spectral component has a wavelength from 100 nm to 2,000 nm. In another exemplary spectrometer embodiment, a back-thinned CCD array is configured to detect at least one spectral component having a wavelength from 150 nm to 400 nm, array apertures have diameters from about 200 nm to about 2,000 nm, the scatter layer has a thickness typically from about 3 µm to about 25 µm and comprises deposited and sintered MgF$_2$ particles having an average diameter of ~600 nm. Another exemplary spectrometer, configured to detect at least one scattered spectral component having a wavelength from 150 nm to 400 nm, has array apertures having diameters from about 75 nm to about 1,600 nm and a scatter layer having a thickness from about 3 µm to about 30 µm and comprising MgF$_2$ particles having diameters from about 80 nm to about 1,000 nm.

In still another exemplary spectrometer embodiment, the at least one spectral component has a wavelength from 300 nm to 1,100 nm, array apertures have diameters from about 200 nm to about 3,200 nm, the scatter layer has a thickness typically from about 2 µm to about 25 µm and comprises TiO$_2$ particles having diameters from about 100 nm to about 1,000 nm in a transparent medium comprising PMMA. Another exemplary spectrometer embodiment is configured to detect at least one scattered spectral component having a wavelength from 500 nm to 2,000 nm. In this embodiment, array apertures have diameters from about 400 nm to about 8,000 nm and the scatter layer has a thickness from about 5 µm to about 50 µm and comprises SiO$_2$ particles having diameters from about 1,500 nm to about 5,000 nm.

In another exemplary spectrometer embodiment, a CCD or CMOS detector array is configured for detecting electromagnetic radiation having wavelengths from 400 nm to 800 nm. In this example, apertures in the aperture array may have diameters ranging from about 400 nm to about 4,000 nm. Exemplary useful scattering medium may comprise TiO$_2$ particles having average radii of ~200 nm in a transparent medium comprising PMMA. The thickness of the scatter layer is typically from about 3 µm to about 25 µm in this exemplary embodiment.

In yet another exemplary spectrometer embodiment, a detector array comprising a focal plane array is configured for detecting electromagnetic radiation having wavelengths from 1 µm to 20 µm. Another exemplary spectrometer embodiment is configured to detect scattered electromagnetic radiation having wavelengths from 5 µm to 20 µm. In this example, apertures in the aperture array may have diameters ranging from about 5 µm to about 200 µm. The scatter layer has a thickness from about 25 µm to about 200 µm and comprises ZnS scatterer particles having diameters from about 500 nm to about 10,000 nm.

Still another exemplary spectrometer embodiment is configured for detecting electromagnetic radiation having wavelengths from 2 µm to 10 µm. In this example, apertures in the aperture array may have diameters ranging from about 2 µm to about 100 µm. The scatter layer comprises ZnS scatterer particles having diameters from about 200 nm to about 5,000 nm and is from about 10 µm to about 100 µm in thickness In still another exemplary embodiment, a spectrometer having a detector array comprising an InGaAs focal plane array is configured for detecting electromagnetic radiation having wavelengths from 900 nm to 1,800 nm. In this example, apertures in the aperture array may comprise diameters ranging from about 900 nm to about 9,000 nm. An exemplary useful scatter layer comprises deposited and sintered SiO$_2$ particles having average diameters of ~3,300 nm. The thickness of the scatter layer is typically from about 15 µm to about 150 µm in this exemplary embodiment.

In another exemplary embodiment, a spectrometer having a detector array comprising an HgCdTe focal plane array is configured for detecting electromagnetic radiation comprising wavelengths from 3 µm to 5 µm. In this example, apertures in the aperture array may comprise diameters ranging from about 2.5 µm to about 25 µm. Exemplary useful scattering media comprise deposited and sintered ZnS scatterer particles having average radii of ~1.9 µm. The thickness of the scatter layer is typically from about 15 µm to about 150 µm in this exemplary embodiment.

In another exemplary embodiment, a spectrometer having a detector array comprising a microbolometer array, such as amorphous Si, is configured for detecting electromagnetic radiation comprising wavelengths from 8 µm to 15 µm. In this example, apertures in the aperture array may have diameters ranging from about 7.5 µm to about 75 µm. Exemplary scattering media comprise deposited and sintered ZnSe scatterer particles having average radii of ~3.6 µm. The thickness of the scatter layer is typically from about 25 µm to about 250 µm.

Other exemplary spectrometer embodiments may be configured to detect radiation having wavelengths from about 10 µm to about 20 µm, from about 100 µm to about 2,000 µm, or from about 1,000 µm to about 20,000 µm.

In some aspects of the invention, a mapping spectrometer is part of a camera. In additional aspects of the invention, a mapping spectrometer comprises a substrate onto which it is affixed. In still further aspects of the invention, a substrate comprises an integrated circuit.

Embodiments of the invention also include methods for analyzing one or more than one spectral components of electromagnetic radiation and methods for producing hyperspectral or spectral images by using various embodiments of the spectrometer of the invention. Methods for analyzing one or more than one spectral components of electromagnetic radiation, for example with a mapping spectrometer of claim 1, comprise receiving electromagnetic radiation through the array of apertures to the scatter layer, through the scatter layer, and thence to the detector array; acquiring data from a speckle pattern produced on the detector array by the one or more than one spectral components of the radiation; and, computationally identifying the one or more than one spectral components of the radiation based on the speckle pattern data. In additional embodiments speckle pattern data are used to produce a spectral or hyperspectral image. In further embodiments of the invention, methods for analyzing radiation further comprise concentrating the electromagnetic radiation prior to passage of the radiation through the apertures. In additional embodiments, methods comprise identifying the polarization state of the one or more than one spectral components of the radiation and/or identifying spatial information about the electromagnetic radiation. In some embodiments, methods for producing hyperspectral images include a spectrometer calibration step. In additional embodiments, computationally identifying one or more spectral components of an image includes implementing an algorithm using information obtained from a calibration step and information obtained from a speckle pattern on a detector array. In some aspects of the invention, the mapping spectrometer comprises or is in communication with a computing device that is configured to receive speckle pattern data or other data from the detector array and process it by implementing an algorithm. In additional embodiments a hierarchical algorithm may be used to computationally identify low-resolution spectral components prior to computationally identifying high-resolution spectral components. Speckle pattern data may be transferred to a processor, buffer, or storage device and in some aspects transfer may be via a communication interface. Additional embodiments of the invention include identifying mineral, biological, chemical species, or man-made objects using speckle pattern data obtained during use of various embodiments of the mapping spectrometer of the invention.

Other embodiments and exemplary embodiments of the invention are discussed throughout this application. However, embodiments of the invention are not limited to the exemplary embodiments described herein. Embodiments described herein are understood to be applicable to all aspects of the invention. It is contemplated that any embodiment discussed herein can be implemented with respect to any method or composition of the invention, and vice versa. Furthermore, compositions of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one." The use of the term "at least one" in the specification and claims is meant to include "one or more than one" and "one or more".

Throughout this application, including in the claims, the symbol "~", which means "approximately" and the term "about" indicate that a value includes plus or minus 25% of the value. For example, "about 4" or "~4" means from 3-5 inclusive, and "about 1 nm" means from 0.75 nm to 1.25 nm inclusive. As used herein, the term "equal" and it's relationship to the values or characteristics that are "substantially equal" would be understood by one of skill in the art. Typically, "substantially equal" means that the values or characteristics referred to may not be mathematically equal but would function as described in the specification and/or claims. All size ranges described herein are inclusive of the lower and upper limit values.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The citation of any references herein is not an admission that such references are prior art for the present invention. It should be understood that the detailed description and the specific examples, while indicating specific embodiments of the invention, are given by way of illustration only, since various changes and modifications within the spirit and scope of the invention will become apparent to those skilled in the art from this detailed description. Other objects, features and advantages of the present invention will become apparent from the following detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 8 shows exemplary scatterers, approximate scatterer dimensions, scatter layer media and approximate dimensions, and detector arrays for detecting radiation in several different ranges of the electromagnetic spectrum, and calculated spectral resolving power across the band using a diffusive theory of light. Resolving power is a dimensionless value. All other units are shown in the table.

DETAILED DESCRIPTION

Figure 1:
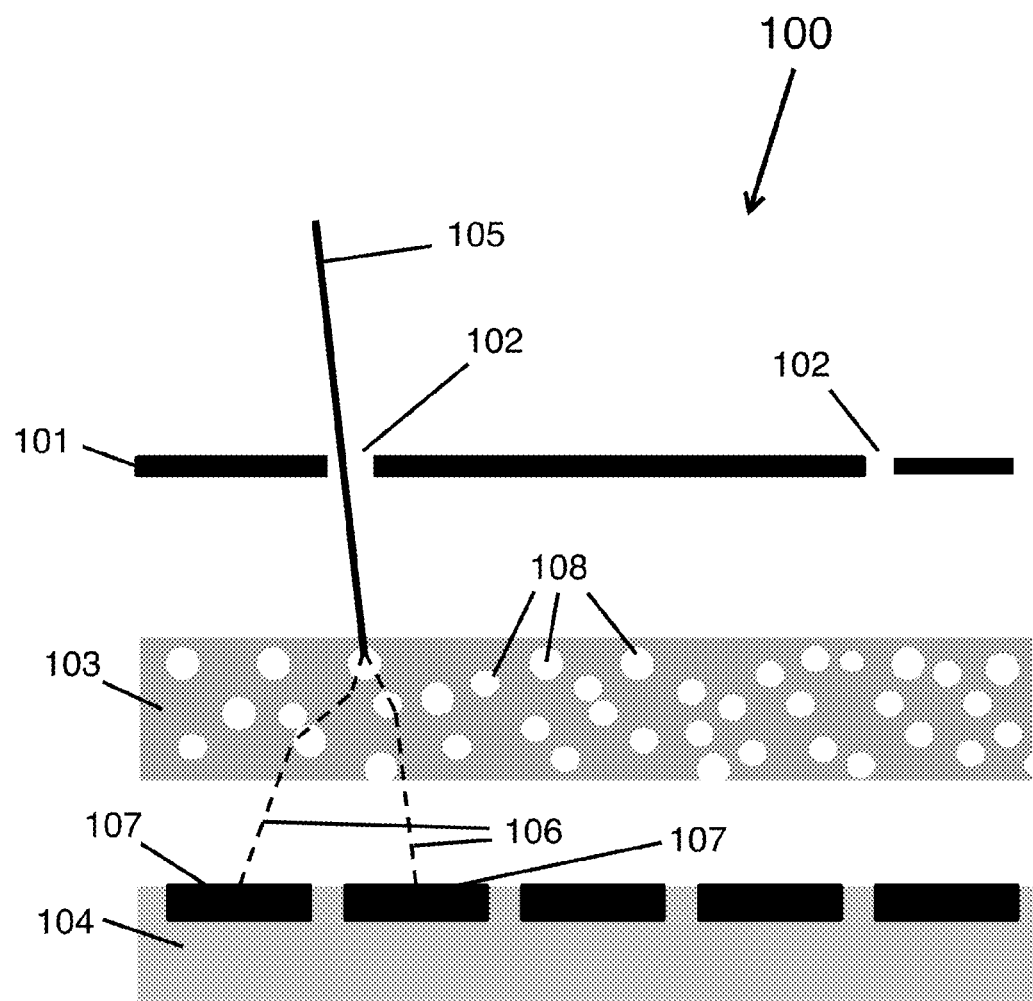
FIG. 1 shows a schematic side view of one embodiment of a mapping spectrometer of the invention and the separation of spectral components of incident radiation.

FIG. 1 shows a schematic side view of one embodiment of a mapping spectrometer of the invention and the separation of spectral components of incident radiation. In this embodiment, spectrometer 100 comprises aperture array 101 having a plurality of apertures 102, detector array 104, and scatter layer 103 positioned between aperture array 101 and detector array 104. Incident radiation 105 passes through aperture 102 before entering scatter layer 103. Radiation 105 is then separated into spectral and/or polarization components 106 (representing different wavelengths and/or polarizations of radiation) by scatter layer 103. In this exemplary embodiment scatter layer 103 comprises scatterers 108 that are distributed throughout the scatter layer. After interacting with scatterers 108, different spectral components 106 follow different scattering pathways to detector array 104 and illuminate a set of pixels 107 producing a reproducible speckle pattern on detector array 104. For calibration, a measurement of the speckle pattern for monochromatic radiation produces a basis vector for the corresponding wavelength. After calibration, the spectrum of radiation passing through the aperture array can be reconstructed using algorithms and predetermined speckle pattern basis vectors.

In some embodiments of the invention, aperture array 101 comprises a plurality of apertures 102. In some embodiments of the invention, apertures may have diameters that range in size from about one-tenth times the length of the shortest wavelength of the at least one spectral component to be detected to about one hundred times the length of the longest wavelength of the at least one spectral component to be detected. That is, apertures have diameters that are about ≥0.1× the length of the shortest wavelength of the at least one spectral component to be detected and about ≤100× the length of the longest wavelength of the at least one spectral component to be detected. In other embodiments of the invention, aperture diameters have sizes that range from about one-tenth times the length of the shortest wavelength of the at least one spectral component to be detected to about ten times the length of the longest wavelength of the at least one spectral component to be detected. In still further embodiments of the invention, an array of apertures comprises apertures having diameters that are from about one-half times the length of the shortest wavelength of the at least one spectral component to be detected to about to two times the length of the longest wavelength of the at least one spectral component to be detected. Smaller aperture sizes are useful for overcoming potential adverse effects associated with incident radiation arriving from various positions and angles (i.e., the apertures spatially filter the incident radiation). However, the amount of incident radiation passing through apertures 102 (i.e., radiative throughput) may be reduced by apertures with smaller diameters. Therefore for some embodiments, apertures having larger diameters are preferred.

Figure 2:
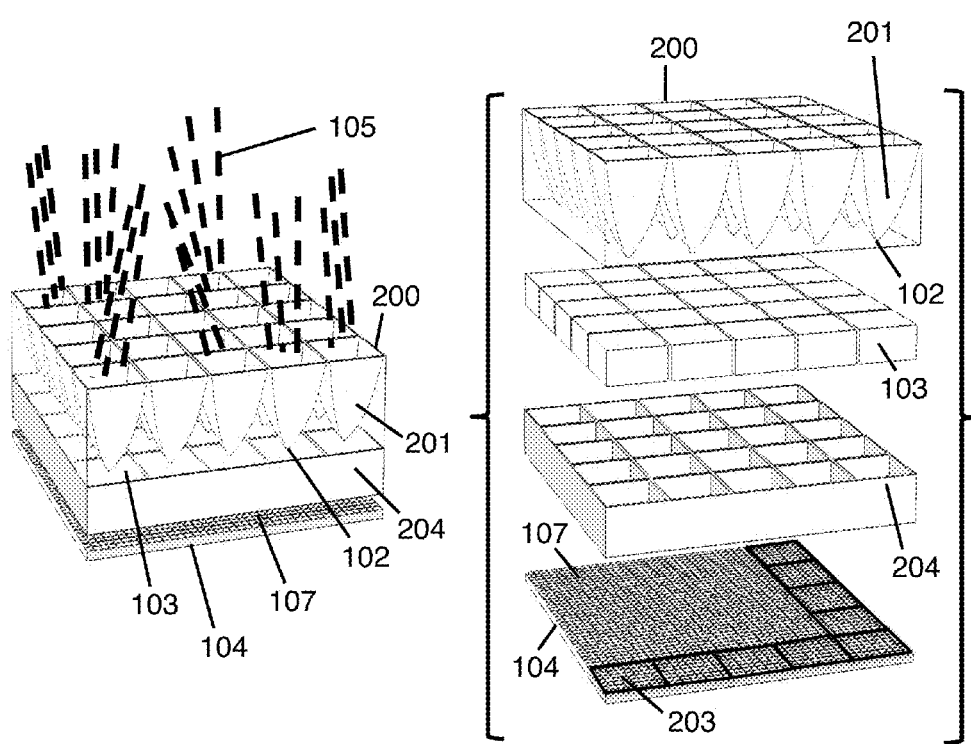
FIG. 2 shows a schematic view and an exploded view of an embodiment of a mapping spectrometer of the invention comprising concentrators integrated with apertures. For simplicity of viewing, only selected scene elements 203 are highlighted in the exploded view.

FIG. 2 shows a schematic view and an exploded view of an embodiment of a mapping spectrometer of the invention comprising concentrators integrated with apertures. For simplicity of viewing, only selected scene elements 203 are highlighted in the exploded view. To enhance radiative throughput and to further homogenize incident radiation, some embodiments of the mapping spectrometer as shown in FIG. 2 comprise an optional array 200 of radiation concentrators 201 positioned between incident radiation 105 and apertures 102. Concentrators 201 gather, homogenize, concentrate, and direct radiation 105 to apertures 102, thereby creating bright point sources of radiation at the exit of apertures 102. Homogenization of incident radiation reduces potential input angle biasing of spectral signatures. In the exemplary embodiment shown in FIG. 2, concentrator array 200 comprises concentrators 201 each of which has an aperture 102 present at its apex. Therefore, in this embodiment, concentrator 201 and aperture 102 are said to be integrated. By definition, when concentrators and apertures are integrated, concentrator array 200 and aperture array 101 are integrated as well. In spectrometer embodiments having concentrators, it is apparent that one concentrator 201 is necessarily "associated with" or "in register with" one aperture 102 and concentrates and directs radiation to only that aperture. As used herein with reference to the alignment of concentrators and apertures, the terms "associated", "associated with", "in association with", "in register", "in register with", and "registered" refer to a condition of correct alignment or proper relative position between a concentrator and an aperture, such that one concentrator 201 concentrates and directs radiation to a single aperture 102. After scattering by scatter layer 103, distinct spectral and/or polarization components 106 (as depicted in FIG. 1) illuminate specific pixels 107 on detector array 104 producing unique speckle patterns on the detector array.

In some embodiments of the invention, fewer than all the apertures in an aperture array are associated with concentrators. That is, some apertures 102 in aperture array 101 do not have concentrators positioned between incident radiation 105 and apertures 102. Any number of apertures 102 in an aperture array 101 may or may not have associated concentrators 201.

A scene element 203 is defined as the set of pixels 107 that may be illuminated by separated spectral components of radiation 105 that has passed through a single aperture 102 (FIG. 2). A scene element may also be referred to herein as a superpixel. A subset of scene elements 203 is highlighted on detector array 104 in FIG. 2. Optional scene element isolators 204 surround selected regions of the scatter layer 103, defining the boundaries of scene elements 203. Scene element isolators 204 are configured to prevent scattered spectral components of radiation from illuminating adjacent scene elements on the detector array that are associated with a different aperture. In some embodiments of the invention, scene element isolators have reflective surfaces.

Figure 3:
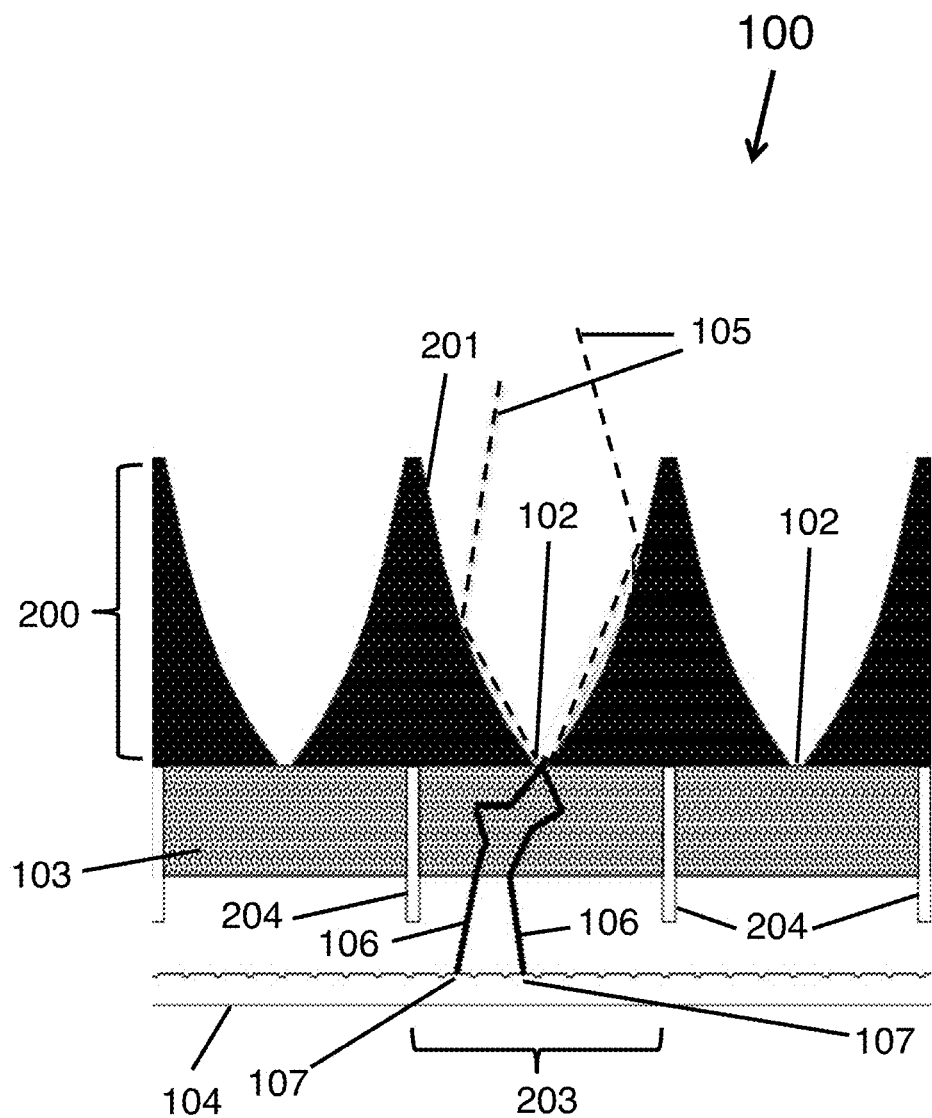
FIG. 3 is a side schematic view of an embodiment of a mapping spectrometer of the invention comprising concentrators integrated with apertures and a schematic depiction of the concentration and separation of spectral components of incident radiation.

FIG. 3 is a side schematic view of an embodiment of a mapping spectrometer of the invention comprising concentrators integrated with apertures and a schematic depiction of the concentration and separation of spectral components of incident radiation. Mapping spectrometer 100 of the invention comprises concentrators 201 integrated with apertures 102. Shown in this figure are a schematic depiction of the concentration of incoming electromagnetic radiation 105 by concentrators 201, the separation of spectral components 106, and the subsequent illumination of pixels 107 in a scene element 203 bounded by scene element isolators 204. Concentrator 201 gathers, homogenizes, concentrates, and directs incident electromagnetic radiation 105 to aperture 102 at the apex of the concentrator. The result is a high-intensity, spatially-filtered point-source of radiation exiting concentrator 201 and passing through aperture 102, thereby enabling reproducible speckle patterns, high radiometric efficiency, and high signal-to-noise ratios for hyperspectral sensing. In some embodiments of the invention the concentrator array defines the angular acceptance of the mapping spectrometer, providing optimal radiometric matching of the spectrometer to external optics. Radiation exiting aperture 102 enters scatter layer 103 and is resolved into spectral components 106, which illuminate pixels 107 on detector array 104.

Figure 4:
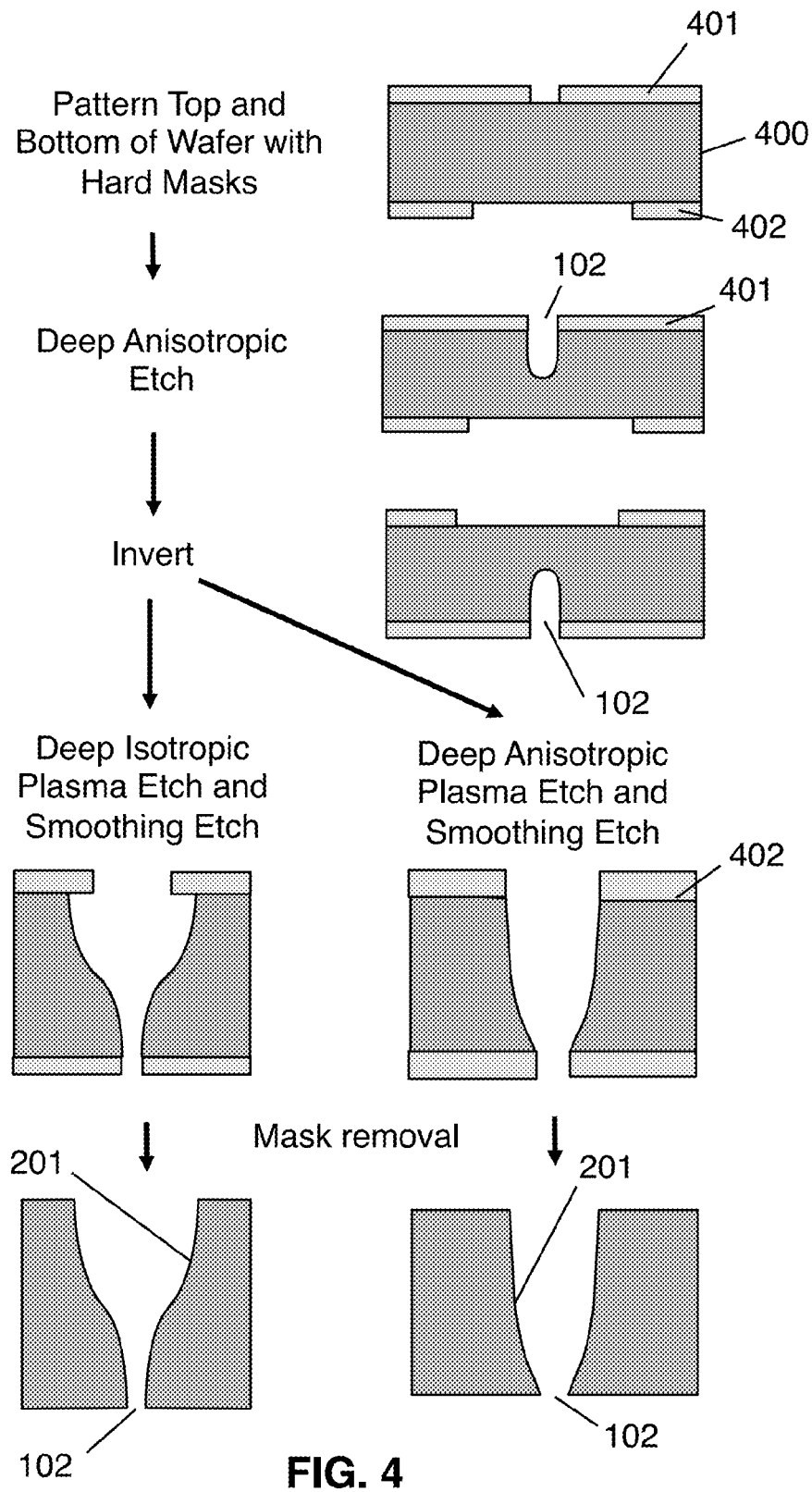
FIG. 4 is a schematic depiction of an exemplary method for fabricating concentrators having integrated apertures.

A concentrator 201 integrated with an aperture 102 may be fabricated by any of a variety of methods. FIG. 4 is a schematic depiction of an exemplary method for fabricating concentrators having integrated apertures. One exemplary method for preparing a concentrator 201 comprising an integrated aperture 102 is shown. By way of example only, standard lithographic and microfabrication techniques known to those with skill in the art allow the construction of many concentrators at one time with accurate placement of each in an array. Illustrated in this figure is the fabrication of a single concentrator 201 comprising an integrated aperture 102. In this method, wafer 400, such as for example a silicon wafer, is patterned with top hard mask 401 and bottom hard mask 402. Aperture 102 is formed using a deep anisotropic etch through top hard mask 401. The wafer is then inverted and an anisotropic or isotropic etch is performed through bottom hard mask 402 to create the general shape of the concentrator 201. Finally, a smoothing etch is performed followed by optional mask removal.

In some aspects of the invention, metallization of concentrators may be desirable, for example to improve the reflectance of concentrator 201. Metallization may be performed following the mask removal shown in FIG. 4. Exemplary metals useful in embodiments of the invention include gold and aluminum. However, other metals may also be used for homogenizing, reflecting, and directing radiation toward aperture 102. A concentrator may be metallized by any of a variety of methods. By way of example only, a concentrator array may be placed in a thermal evaporator with a rotating stage to provide uniform coverage of concentrators with the selected metal. Alternately, plasma-assisted sputtering or atomic layer deposition may be performed to produce a uniform metal layer, or a dip-method, such as electroless nickel plating, may be used. In other aspects of the invention, metallization of concentrators is not required or preferred, such as for example when a concentrator is designed to function in a total internal reflection mode or when a concentrator array is an array of lenses or an array of tapered transparent media.

Figure 5:
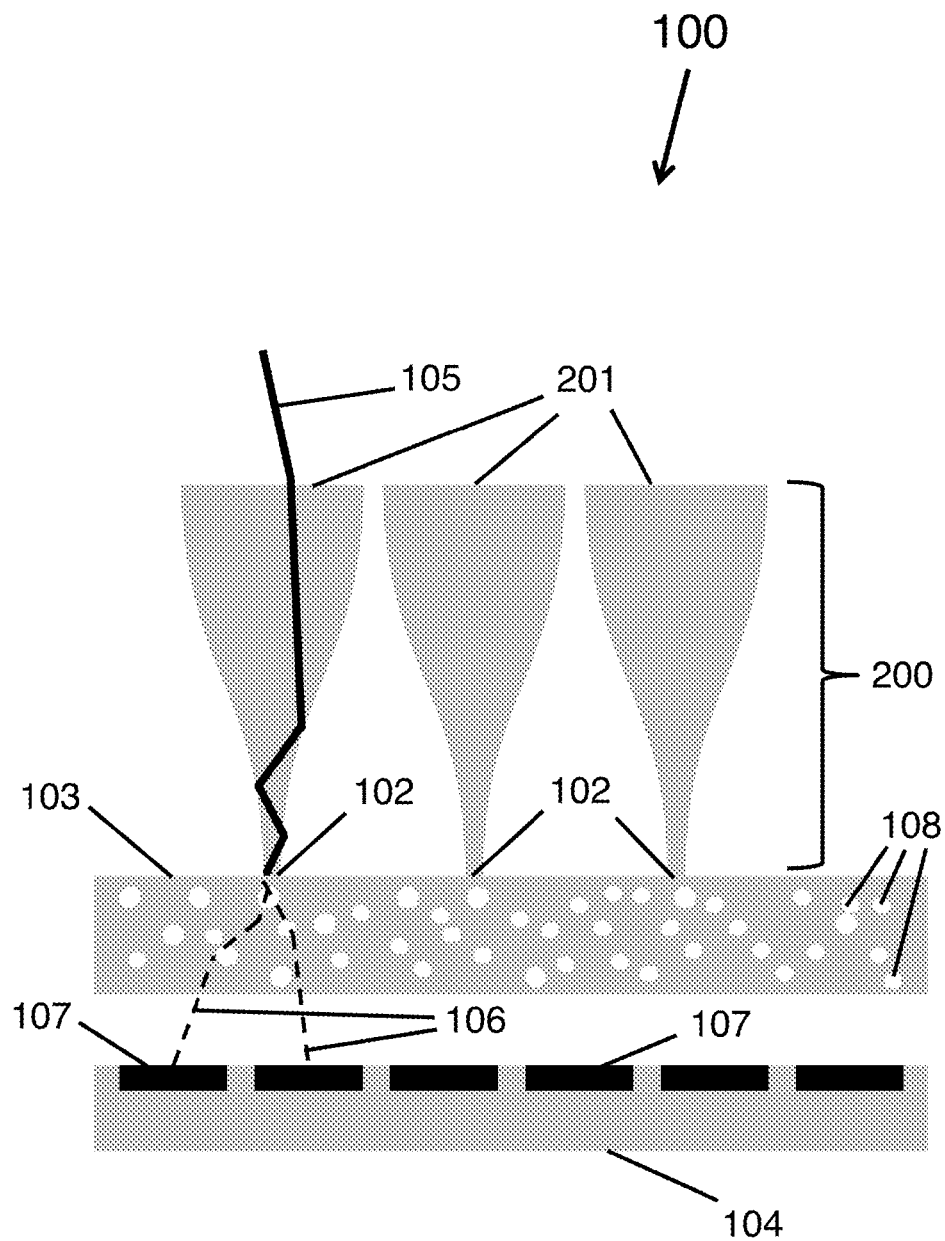
FIG. 5 is a side schematic view of another exemplary embodiment of a mapping spectrometer of the invention having a concentrator array of tapered total internal reflection concentrators 201 having integrated apertures 102.

FIG. 5 is a side schematic view of another exemplary embodiment of a mapping spectrometer of the invention having a concentrator array of tapered total internal reflection concentrators 201 having integrated apertures 102. Also shown is a schematic depiction of the separation of spectral components of incident radiation. Depicted is an array 200 of concentrators 201 that comprise tapered transparent media having inner surfaces that are reflective to electromagnetic radiation either by total internal reflection or by having external metallic or dielectric coatings so as to cause internal reflection of the radiation. Concentrators 201 comprise apertures 102 at the tapered ends. In this embodiment, tapered transparent media gather, homogenize, concentrate, and direct incident electromagnetic radiation 105 to aperture 102 at the tapered end of the transparent media. Radiation exiting aperture 102 enters scatter layer 103 comprising scatterers 108 and is separated into spectral components 106, which illuminate pixels 107 on detector array 104.

One exemplary method of preparing aperture array 101 uses deposition of an electromagnetic radiation blocking (non-transmitting) layer onto a transparent substrate and subsequently etching or otherwise removing the material to form apertures 102. For example, for use with electromagnetic radiation in the visible wavelength range, such a method would comprise the steps of depositing 100 nm-500 nm of aluminum onto a glass wafer, spin-coating a resist layer to protect the aluminum, selectively removing resist at the intended locations of the apertures, dipping the wafer with aluminum in an etchant to produce the apertures, and removing the resist layer.

Figure 6:
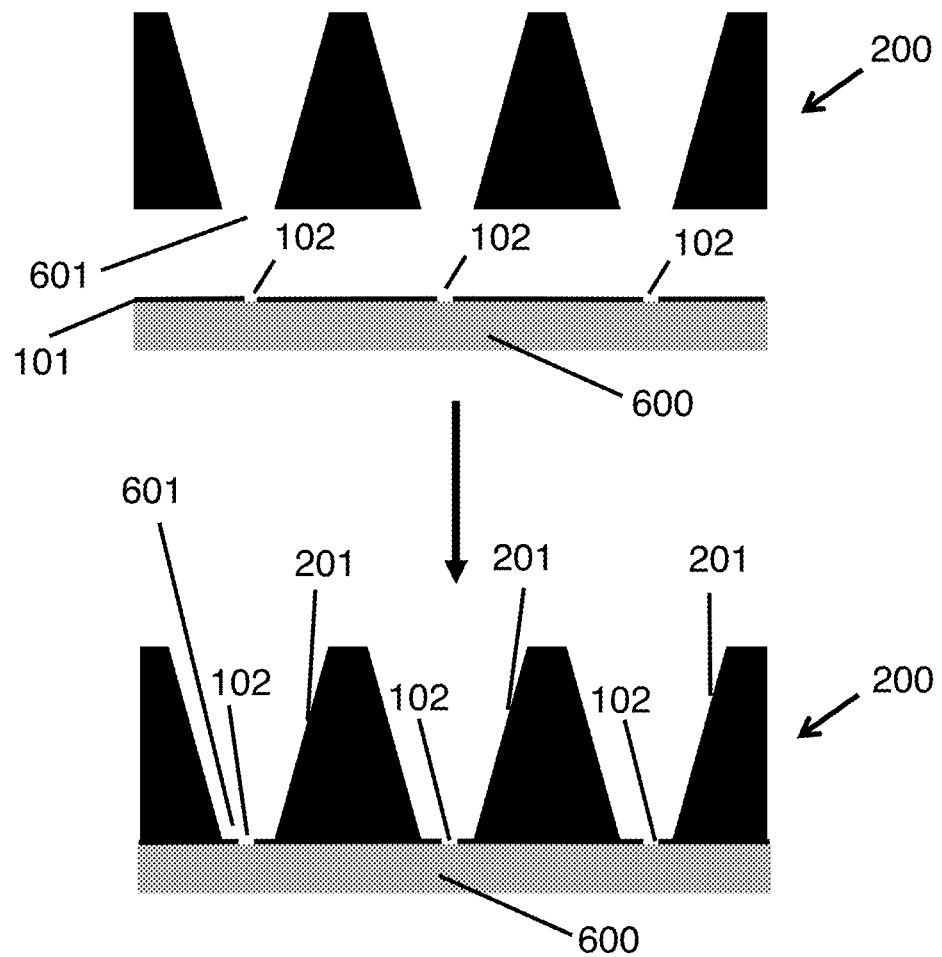
FIG. 6 is a side view of a schematic depiction of the assembly of a concentrator array and an aperture array in a non-integrated configuration.

FIG. 6 is a side view of a schematic depiction of the assembly of a concentrator array and an aperture array in a non-integrated configuration. In some spectrometer embodiments, concentrator array 200 and aperture array 101 are separate elements (not integrated), and concentrator 201 comprises a concentrator exit 601, as shown in FIG. 6, to allow for passage of radiation from the concentrator 201 to aperture 102. Mapping spectrometers of the invention having a concentrator array that is not integrated with an aperture array are also configured such that one concentrator is associated with one aperture 102 of aperture array 101, and radiation entering a single concentrator 201 is directed to a single aperture 102 of the aperture array that is in register with or associated with that concentrator. In some embodiments of the invention, aperture array 101 comprises a plurality of apertures 102. Similarly, concentrator array 200 comprises a plurality of concentrators 201. In this example, aperture array 101 comprising apertures 102 is manufactured with an optional aperture array support 600. Concentrator array 200 is manufactured separately. Concentrator array 200 and aperture array 101 are assembled and aligned in a configuration that associates a single concentrator 201 with a single aperture 102, positioned so that radiation can pass from concentrator 201 through concentrator exit 601, thence through aperture 102.

Concentrators 201 useful in embodiments of the invention need not be tapered non-imaging structures. Other radiation-gathering concentrators, radiation collectors, optical elements, and non-optical elements or structures may be useful as concentrators in embodiments of the invention, and concentrators need not have curved sides. Concentrators may be any shape useful for gathering, homogenizing, concentrating, and directing radiation to apertures 102. For example, concentrator 201 may have straight sides and may be a conical frustum or a pyramidal frustum, with a circular or square cross section, respectively. An exemplary useful embodiment of concentrator has a cross section that transitions from rectangular at the opening to elliptical at the exit. This embodiment has efficient fill factor for arrays of concentrators and optimizes the radiative throughput of spectrometer 100. Other embodiments of the invention may comprise concentrators with elliptical or rectangular cross-sections and a taper function designed to maximize light collection efficiency when coupled with specific imaging optics having a known etendue. In some embodiments, concentrators have a compound parabolic shape. In some aspects of the invention concentrators are "open structures", such that incoming radiation enters an open end of the light gathering concentrator. Concentrators that are open structures typically comprise one end that is distal to the aperture array and another end that is proximal to the aperture array. It is not a requirement that concentrators useful in embodiments of the invention be "open" structures. In some aspects of the invention, concentrators may be lenses or other optical elements, or combinations of these that are capable of homogenizing radiation and directing radiation to apertures on an aperture array. For example an array of concentrators may comprise an array of concentrating lenses configured to concentrate electromagnetic radiation to an aperture array.

In additional embodiments of the invention, an array of concentrators may comprise more than one type of concentrator.

In some embodiments of the invention, such as when aperture array 101 is not integrated with concentrator array 200, the aperture array may comprise a plate or film having an array of apertures extending therethrough. In these embodiments, aperture array 101 is typically fabricated by forming apertures in a reflective or absorbing (i.e., non-transmitting or non-transparent) medium. In some aspects of the invention, aperture array 101 comprises an array of apertures in a layer that is reflective on at least the surface of the aperture array facing the scatter layer. The reflective property is advantageous in that it reflects radiation that has been backscattered by scatter layer 103 back towards the scatter layer 103, thereby increasing radiative throughput. In other aspects of the invention, aperture array 101 may comprise a self-supporting film or thin sheet or strip. Exemplary materials for a self-supporting film include nickel, invar, or other metallic alloys having a desired combination of high melting point, high optical density, and low thermal expansion coefficient. In some mapping spectrometer embodiments of the invention, it may be desirable to provide an aperture array support 600 for aperture array 101, such as in the exemplary embodiment depicted in FIG. 6. The need for an aperture array support 600 will depend on the specific embodiment and application of a mapping spectrometer of the invention. For example, a mapping spectrometer that will be transported to space as a payload on a rocket may need to be more rugged against vibration and temperature changes, and an aperture array support 600 may prove useful with these embodiments. In some aspects of the invention, an aperture array support is transparent over the range of wavelengths of the incident radiation. Exemplary aperture array support materials are glass, sapphire, $CaF_2$, and quartz for use in the UV, VIS, and SWIR spectral regions, and Si, Ge, GaAs and ZnSe for use in the MWIR and LWIR spectral regions. In other aspects of the invention, scatter layer 103 may function as an aperture array support. In still other aspects of the invention, scene element isolators 204 may function as an aperture array support. Aperture array supports may support an aperture array by abutting the array. However, aperture array supports need not be continuous and may support an aperture array from the periphery or edge of a scene element for instance. An aperture array support may be any material that is useful in supporting the aperture array including glass, metals, ceramics, and polymers.

In embodiments of the invention having non-integrated concentrators and apertures, the aperture array is configured such that one aperture 102 is in register with exit 601 of one concentrator 201, allowing for passage of radiation from the concentrator through the aperture 102. In these embodiments, aperture array 101 may abut against concentrator array 200 as in FIG. 6. That is, no gap or space is necessarily present between exit 601 and aperture 102. In other spectrometer embodiments not having an integrated concentrator and aperture, such as for example a spectrometer having a concentrator array that comprises lenses, a gap or space between the concentrator and the aperture may be desirable.

In some embodiments of the invention apertures in an aperture array are arranged in a periodic pattern. An array of apertures may be a one-dimensional (1D) array or a two-dimensional (2D) array.

The shape of an aperture need not be circular. Other aperture geometries may be useful for passing radiation to the scatter layer and for spatially filtering the incident radiation. In some embodiments of the invention, specific aperture shapes, such as for example non-circular ellipses and slits, may be preferred for passing or rejecting specific wavelengths and polarizations of incident radiation. In some aspects of the invention, plasmonically-active apertures may be useful for spatially-filtering incident light. In still other aspects of the invention, an aperture may comprise a plurality of closely spaced but separate apertures.

Apertures in aperture arrays of the invention may vary in diameter. In some embodiments of the invention, an array of apertures comprises apertures having diameters that are substantially equal. In other embodiments of the invention, an array of apertures comprises apertures having diameters that differ among the apertures. In some aspects of the invention, an aperture array may comprise a plurality of groups of apertures wherein the apertures within each group have substantially equal diameters. In some aspects of the invention in which a plurality of aperture groups are present in an array, the apertures within one or more groups may have diameters that differ among each other. It is specifically contemplated that any combination of aperture diameters within and among groups can be used in various aspects of the invention. As used herein in reference to aperture diameters, "substantially equal" means that the aperture diameters have a distribution about the mean diameter with a standard deviation less than 20% of the mean diameter, regardless of the aperture diameter. The choice of aperture diameter will depend on the particular application of a mapping spectrometer and the wavelengths or wavelength ranges of spectral components to be sensed. Aperture arrays comprising a plurality of apertures having different diameters may be useful, by way of example only, in applications that benefit from non-uniform data sampling, for example coded-aperture concepts or spectrometer designs in which different spectral/radiative parameters are required by different portions of the detector.

The useful diameter of an aperture is affected by several factors among which are the wavelengths of the incident radiation that will be scattered, the focal ratio of any imaging optics that may be present and that are directing the incident radiation, the effectiveness of homogenization of the radiation by an optional concentrator that may be present in some embodiments, the makeup and dimensions of the scatter layer, and any gap that may be present between aperture array 101 and scatter layer 103.

In selected exemplary embodiments of the invention, aperture diameters range in size from about one-half to about two times the length of the longest wavelength of electromagnetic radiation to be detected. By way of example only, aperture diameters useful with radiation having wavelengths of 400 nm to 600 nm may range from about 300 nm to about 1,200 nm or larger in diameter. Table 1 shows aperture diameters appropriate for passing radiation of various wavelengths and ranges in the selected exemplary embodiments.

TABLE 1

Exemplary ranges of aperture diameters useful in selected exemplary embodiments of the mapping spectrometer when sensing radiation of various wavelengths.

| Longest Wavelength in Radiation of Interest | Small Aperture Diameter | Large Aperture Diameter |
| --- | --- | --- |
| 20 nm | 10 nm | 40 nm |
| 200 nm | 100 nm | 400 nm |
| 600 nm | 300 nm | 1,200 nm |

TABLE 1-continued

Exemplary ranges of aperture diameters useful in selected exemplary embodiments of the mapping spectrometer when sensing radiation of various wavelengths.

| Longest Wavelength in Radiation of Interest | Small Aperture Diameter | Large Aperture Diameter |
| --- | --- | --- |
| 1.6 μm | 0.8 μm | 3.2 μm |
| 5.2 μm | 2.6 μm | 10.4 μm |
| 14 μm | 7 μm | 28 μm |
| 20 μm | 10 μm | 40 μm |
| 100 μm | 50 μm | 200 μm |

In other embodiments of the invention, and for example only, aperture diameters that are five times larger, ten times larger, one hundred times larger, or up to one thousand times larger than the longest wavelength of radiation to be detected, may be useful for increasing radiative transfer through the aperture, thereby increasing the radiometric efficiency and sensitivity of detection of radiation. In some embodiments of the invention, by way of example only, the aperture diameter may be equal to the longest wavelength of radiation present in incoming radiation 105 multiplied by the focal ratio of the imaging optics divided by 5. As an example, for a mapping spectrometer operational in the MWIR (3 μm-5 μm) operating at f/10, an aperture diameter would be 5 μm×10/5=10 μm. Because the physics of mapping spectrometers of the invention are applicable for sensing and imaging radiation from across the entire electromagnetic spectrum, aperture diameters may vary widely and may be sized accordingly to optimize the performance of spectrometers of the invention in the specific application. A practical upper limit on the aperture size is 1,000 times the longest wavelength of a spectral component of radiation to be detected. In certain aspects of the invention, such aperture diameters are useful in situations in which the smallest spatial variations in the incident radiation have a size that is at least as large as the aperture diameter. By way of example only, an aperture useful with embodiments of a mapping spectrometer for detecting electromagnetic radiation in the SWIR band (0.9 μm-2.0 μm) has a practical upper size limit diameter of 2.0 mm.

Figure 7A:
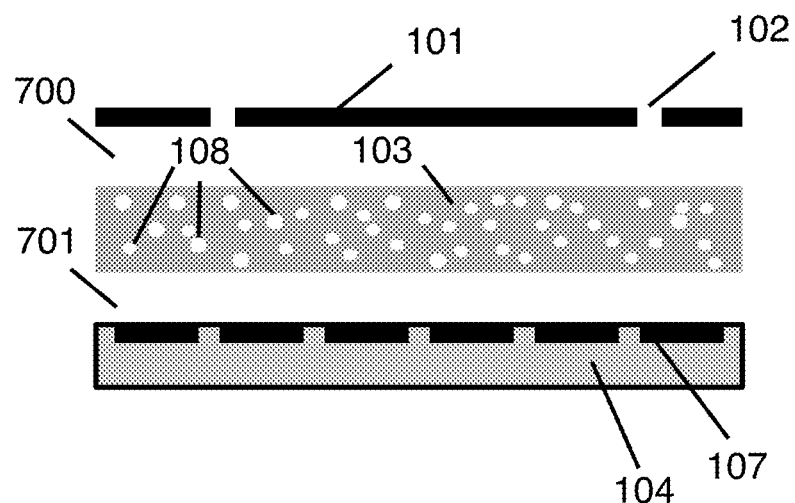
FIG. 7A shows a side schematic view of a mapping spectrometer of the invention having a relatively larger gap 700 or space between aperture array 101 and scatter layer 103 and a relatively larger gap 701 between scatter layer 103 and detector array 104.
Figure 7B:
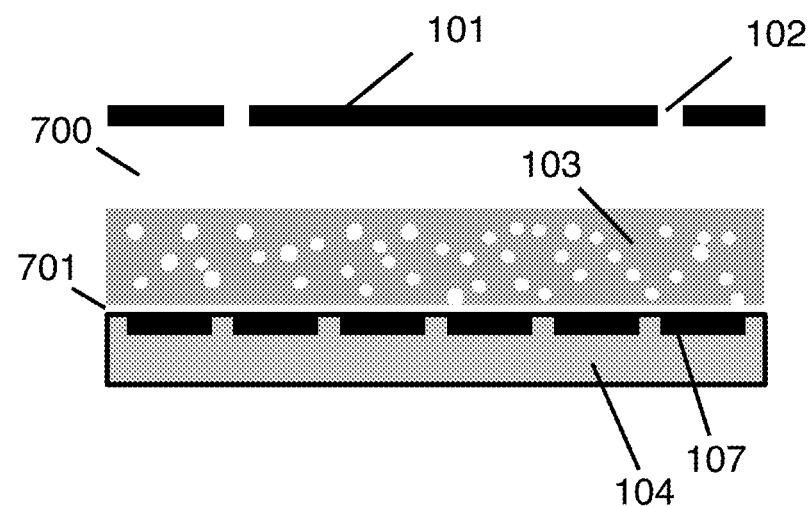
FIG. 7B shows a side schematic view of a mapping spectrometer having a relatively larger gap 700 between aperture array 101 and scatter layer 103 and a relatively narrow gap 701 between scatter layer 103 and detector array 104.
Figure 7C:
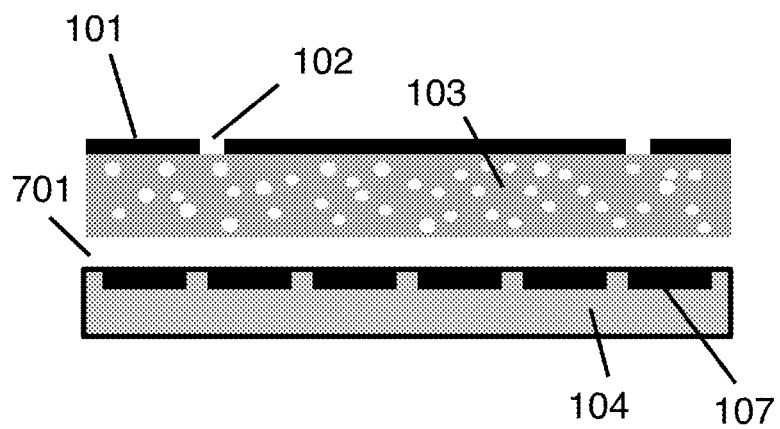
FIG. 7C shows a side schematic view of a mapping spectrometer having no gap between aperture array 101 and scatter layer 103 and a relatively large gap 701 between scatter layer 103 and detector array 104.
Figure 7D:
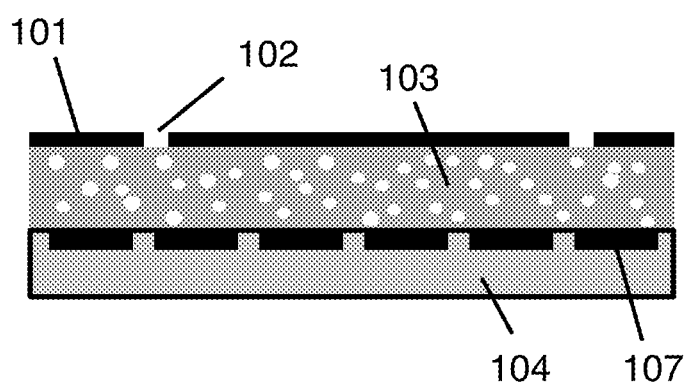
FIG. 7D shows a side schematic view of a mapping spectrometer having no gap between aperture array 101 and scatter layer 103 and no gap between scatter layer 103 and detector array 104.

In some embodiments of the invention, it may be desirable that a gap be present between aperture array 101 and scatter layer 103, such as for example to reduce the possibility of radiation backscattering though aperture 102. In additional embodiments of the invention it may be desirable that a gap be present between scatter layer 103 and detector array 104. FIG. 7A shows a side schematic view of a mapping spectrometer of the invention having a relatively larger gap 700 or space between aperture array 101 and scatter layer 103 and a relatively larger gap 701 between scatter layer 103 and detector array 104. FIG. 7B shows a side schematic view of a mapping spectrometer having a relatively larger gap 700 between aperture array 101 and scatter layer 103 and a relatively narrow gap 701 between scatter layer 103 and detector array 104. FIG. 7C shows a side schematic view of a mapping spectrometer having no gap between aperture array 101 and scatter layer 103 and a relatively large gap 701 between scatter layer 103 and detector array 104. FIG. 7D shows a side schematic view of a mapping spectrometer having no gap between aperture array 101 and scatter layer 103 and no gap between scatter layer 103 and detector array 104. For simplicity of viewing, scatterers 108 are only labeled in FIG. 7A. These embodiments may be useful for maximizing the point source radiation passing through aperture 102 to scatter layer 103, thereby improving separation of spectral components 106 and resolution.

In some embodiments of the invention, gap 701 between scatter layer 103 and detector array 104 may range from >0 μm to about 200 μm. In other embodiments, especially for longer-wavelength spectral regions gap 701 ranges from >0 μm to about 1,500 μm. Larger detector arrays may require a relatively larger gap (depicted schematically in FIG. 7A, FIG. 7C) to circumvent damage from contact between scatter layer 103 and detector array 104, and smaller detector arrays may require a relatively smaller gap 701 (FIG. 7B) or no gap (FIG. 7D). Detectors that may be subjected to rougher treatment or deployed in more harsh environments may have a larger gap 701 between the scatter layer and the detector array to reduce the likelihood of damaging the detector array. In some embodiments of the invention, such as when a scene element comprises a large number of pixels, a larger gap size may be advantageous. It will be apparent that the size of gap 701 may be adjusted depending on the application of the detector, the type of detector array employed, the size of the detector array, and other factors such as, for example, the likelihood of thermal expansion during employment. In some aspects of the invention, the distance between the aperture array and the detector array is from 1 nm to 1 cm inclusive.

In some embodiments of the invention, scatter layer 103 comprises a first surface also referred to as a first "side" facing aperture array 101 and a second opposing surface or side facing detector array 104. In some aspects of the invention, scatter layer 103 may comprise anti-reflection coatings or treatments applied to one or both sides of the scatter layer in order to maximize the transmission of radiation through scatter layer 103. Enhanced radiation transmission toward detector array 104 may be realized when scatter layer 103 comprises an anti-reflective coating, on the side of scatter layer 103 facing detector array 104 or on the side of scatter layer 103 facing aperture array 101, and aperture array 101 comprises a reflective coating on a surface facing scatter layer 103. Anti-reflection coatings may be thin film dielectric stacks, graded-index structures including motheye-like structures, and quarter wave plates that are well known in the art.

Mapping spectrometers of the invention use scattering of electromagnetic radiation from certain structures, disordered media, or other scatterers for the purpose of separating the spectral and/or polarization components 106 of incoming radiation 105 prior to detection by detector array 104. The pattern of pixel illumination produced on detector array 104 by electromagnetic radiation that has passed through an aperture and been scattered by scatter layer 103 is referred to as a speckle pattern. The uniqueness of speckle patterns produced by different spectral components 106 is exploited to effect the spectral resolution of the invention.

In some spectrometer embodiments of the invention, scatter layer 103 comprises a medium that is translucent or transparent to one or more spectral components 106 of incoming radiation 105. Scatter layer 103 effects separation of spectral components by virtue of different scattering behavior exhibited by different spectral components 106 upon interaction with the scatter layer medium or with scatterers 108 that may be present within or on the scatter layer medium or scatterers that are structural variations within or on the scatter layer medium. In some aspects of the invention, a scatter layer comprises one or more types of scatterers 108 that interact with incoming radiation, effecting the separation of spectral components of the radiation.

Scatterers 108 may take several forms, including for example intentionally-disordered structures, random mixtures of distinct materials, particles, self-assembled structures, and patterned surfaces. Scatterers may be surface relief structures present on a surface of a scatter layer medium or a scene element isolator. Scatter layer 103 may comprise a thin metal film that is a scatterer. Scatterers may also be metal particles, ceramic particles, fibers, voids, surface relief structures, or other inhomogeneities that are present on or dispersed in a scatter layer medium. Scatterers that are particles are also referred to herein as "scatterer particles". Scatter layer 103 may comprise one or more type or form of scatterer 108.

In some embodiments of the invention, a scatter layer may comprise scatterers that are not suspended in or on the surface of a medium. In some aspects of the invention, scatterers may be present as agglomerations, such as an agglomeration of particles, without a medium. It is not a requirement that a scatter layer be a continuous layer. In some embodiments of the invention, the scatter layer is discontinuous and may comprise, by way of example only, an agglomeration of particles or a section of metal film that is present between an aperture and the detector array and that does not have the form of a continuous layer extending entirely across a detector array. In some aspects of the invention, a discontinuous scatter layer may extend across a single aperture or across a plurality of apertures. Scatter layer 103 depicted in FIG. 2 is one example of a discontinuous scatter layer. In this exemplary embodiment, scene element isolators 204 separate individual sections of scatter layer 103, such that the scatter layer is discontinuous and comprises scatterers between each integrated aperture 102 and detector array 104. In some aspects of the invention, a scatter layer need not entirely fill the region that is surrounded by a scene element isolator 104. Discontinuous scatter layers may comprise any material described herein as being useful for scattering spectral components of incoming radiation and may be any size or shape that is compatible with a spectrometer embodiment and that functions to scatter spectral components of radiation. In some embodiments of the invention, the scatter layer thickness is from 1 nm to 1 cm inclusive.

In some embodiments of the invention, scatter layer 103 comprises a transparent medium having surface relief structures that are scatterers 108. Examples of surface relief structures include protrusions and depressions that may be in the form of grooves, bumps, pits, nodules, gratings, and other structures useful for the separation of different wavelengths and polarizations of light. After passage through aperture 102, each spectral component 106 of incident radiation 105 interacts differently with the surface relief structures on the scatter layer medium. Surface relief structures may be applied to or made on one or more sides or surfaces of a scatter layer medium forming scatter layer 103. Surface relief structures may be formed, by way of example only, by at least one of etching, impacting with abrasive material, material deposition, or lithography. In some embodiments of the invention, surface relief structures may be spatially repetitive tilings of a single structure or group of structures, or may be applied randomly to a side or surface of a scatter layer medium.

In some aspects of the invention, the transparent medium having surface relief structures may comprise one or more acrylics including PMMA, polyamides including nylon, polyvinyls, polycarbonates, polystyrenes, silanes, polydimethylsiloxane, polypropylenes, polyimides, polymethylpentene, fluoropolymers, polyesters, optical epoxies, stilbene, ceramics including $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, CdTe, ZnS, ZnSe, diamond, Si, Ge, $Ba(NO_3)_2$, BBO, KDP, $LiNbO_3$, ZGP, LiF, CsI, NaCl, KBr, AlN, $Si_3N_4$, SiC, and metals including Al, Ag, Au, B, Be, Be, Co, Cu, Fe, Mg, Mo, Nb, Ni, Pb, Pd, Pt, Rh, Ta, Ti, V, Zn, and Zr. Other optical materials known to those of skill in the art may be useful as transparent media and will become apparent from this description of the invention. Some exemplary methods for forming surface relief structures on scatter layer 103 include chemical or plasma etching, material deposition, impact with abrasive materials, imprinting or embossing, and lithographic processes. Surface relief structures on scatter layer 103 may also have periodic structures, producing a special type of coherent scattering known as diffraction. Diffraction, diffraction gratings, and their ability to separate spectral components of radiation are known to those with skill in the art. In the present invention, diffraction gratings with a constant grating vector, radial gratings, azimuthal gratings, or superpositions or spacing modulations of diffraction gratings could be used to separate spectral components 106.

In other embodiments of the invention, scatter layer 103 comprises a metal film. In some aspects of the invention, a metal film may comprise one or more of Be, Al, and Si. Metal films useful as scatter layers in spectrometers of the invention may range from 5 nm to 5,000 nm. In other embodiments of the invention a metal film scatter layer may range from 20 nm to 200 nm in thickness.

In still other embodiments of the invention, scatter layer 103 may comprise scatterers 108 that are particles distributed in a transparent or translucent scatter layer medium or an agglomeration of particles in a medium. Exemplary transparent media for use with scatterers include acrylics including PMMA, polyamides including nylon, polyvinyls, polycarbonates, polystyrenes, silanes, polydimethylsiloxane, polypropylenes, polyimides, polymethylpentene, fluoropolymers, polyesters, optical epoxies, stilbene, $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, CdTe, ZnS, ZnSe, diamond, Si, Ge, $Ba(NO_3)_2$, BBO, KDP, $LiNbO_3$, ZGP, LiF, CsI, NaCl, KBr, AlN, $Si_3N_4$, SIC, and for the soft x-ray and vacuum ultraviolet may include Al, Ag, Au, B, Be, Be, Co, Cu, Fe, Mg, Mo, Nb, Ni, Pb, Pd, Pt, Rh, Ta, Ti, V, Zn, and Zr.

In further embodiments of the invention, a scatter layer 103 may comprise scatterers 108 that are an agglomeration of particles that are fused or sintered in the absence of a surrounding scatter layer medium. Exemplary scatterer particles that may be present in scatter layer 103 include one or more types of metal particles, such as for example Al, Ag, Au, B, Be, Be, Co, Cu, Fe, Ge, Mg, Mo, Nb, Ni, Pb, Pd, Pt, Rh, Si, Ta, Ti, V, Zn, and Zr, and one or more types of ceramic particles, such as for example $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, CdTe, ZnS, ZnSe, diamond, Si, Ge, $Ba(NO_3)_2$, BBO, KDP, $LiNbO_3$, ZGP, LIF, CsI, NaCl, KBr, AlN, $Si_3N_4$ and SIC.

An exemplary scatter layer 103 useful for separating radiation having wavelengths in the visible range of the spectrum may comprise scatterer particles of one or more of $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, ZnS, ZnSe, diamond, BBO, KDP, $LiNbO_3$, LIF, CsI, NaCl, KBr, AlN, $Si_3N_4$ and SIC, borosilicate glass, barium sulfate, or barium titanate dispersed in a transparent polymer, glass, or ceramic binder scatter layer medium. In some embodiments, it is desirable that any scatter layer media do not absorb radiation over the range of wavelengths that are to be detected, and that scatterer particles and the medium exhibit enhanced refractive index contrast (i.e., the refractive index of the particles is different from that of the medium). Suitable exemplary medium materials include acrylics including PMMA, polyamides including nylon, polyvinyls, polycarbonates, polystyrenes, silanes, polydimethylsiloxane, polypropylenes, polyimides, polymethylpentene, fluoropolymers, polyesters, optical epoxies, and stilbene, $Al_2O_3$, $BeO_2$, $GeO_2$, $SiO_2$, $TiO_2$, $Y_2O_3$, $ZrO_2$, MgO, CaO, SrO, BaO, $BaF_2$, $CaF_2$, $MgF_2$, ZnS, ZnSe, diamond, BBO, KDP, $LiNbO_3$, LiF, CsI, NaCl, KBr, AlN, $Si_3N_4$ and SiC, and other optical glasses or transparent crystalline materials. One exemplary scatter layer for use with visible wavelengths of radiation comprises titanium dioxide scatterer particles having average radii of ~300 nm embedded in a transparent polymer medium, such as for example poly(methyl methacrylate) with a weight ratio of 1:1 of PMMA:$TiO_2$, and has a total scatter layer thickness in the range of 3 µm-25 µm.

In additional aspects of the invention, scatter layer 103 may comprise a transparent medium having voids or bubbles containing gas that function as scatterers 108 and that are distributed within the medium. In other aspects of the invention, a transparent scatter medium has structural defects that function as scatterers 108. Structural defects such as inhomogeneities that can scatter and separate wavelengths and/or polarization of light include, for example, crystal dislocations, grain boundaries, inclusions, and density and/or concentration variations. Voids, bubbles, and structural defects and inhomogeneities also have enhanced refractive index contrast with the surrounding medium, i.e., they have a refractive index different from the medium and are thus capable of effecting separation of spectral components 106.

In additional embodiments of the invention, especially for detecting electromagnetic radiation having very short wavelengths (vacuum ultraviolet and X-ray bands), a scatter layer 103 may be a thin film of metal. It is preferred that the thin film be made from metals with a low atomic number, such as for example Be or Al. Metal film thicknesses from 5 nm to 5,000 nm are typically used for these embodiments. Materials like Be, Al, Mo, Si, Ge, Sn, and SiC are also commonly used to produce dielectric stacks and optical filters in the VUV, for instance, and may be employed as scatterers in the invention. Metals with heavier atomic number may also be employed, depending upon the spectral components to be detected and the amount of scattering in relation to absorption that is desired. Some examples of these metals are Al, Ag, Au, B, Be, Be, Co, Cu, Fe, Mg, Mo, Nb, Ni, Pb, Pd, Pt, Rh, Ta, Ti, V, Zn, and Zr. Optical constants may be compiled for candidate materials useful for the VUV and X-ray wavelength ranges by methods known to those of skill in the art.

For detecting electromagnetic radiation in the far infrared and terahertz wavelength ranges, TEFLON® (PTFE), PET, silicon, quartz, and polymethylpentene (PMP or TPX) are common optical materials that may be useful as scatterers. When produced as scatterers with dimensions comparable to the wavelength of light, as further described below, these materials are useful with embodiments of the invention for measuring spectra of electromagnetic radiation having wavelengths in the terahertz range. The requirements for terahertz optics, such as bandpass filters, polarization filters, windows, optics, and detectors including microbolometer arrays, micro Golay cell arrays, forward-biased Schottky barrier diode arrays, semiconductor and superconducting hot electron bolometers, and superlattices are known to those with skill in the art.

The refractive index of a material is only one intrinsic property, and the ultimate selection of scatterers for the invention will rely not only on the optical constants of the materials comprising the scatter layer, but also on the design requirements that may be unique to a specific application. For instance, in low temperature applications where scatterers are in thermal contact with a cooled focal plane detector array, the coefficient of thermal expansion of scatterers may play a less-significant role in the selection of useful scatterers for a particular spectrometer embodiment due to the temperature stability provided by the focal plane array cooling assembly. For spectrometer embodiments intended for a use in a variety of thermal environments, the coefficient of thermal expansion of the scatterers becomes more important to consider, as a change in the scatterer particle spacing can result in changes in speckle patterns. A useful approach to addressing these types of situations includes calibrating the spectrometer for use at a variety of temperature ranges. Another approach includes using scatterers, scatterer particles, or scatter layer media with an extremely small coefficient of thermal expansion, such as quartz. Optical, physical, and mechanical parameters for materials, including thermal expansion coefficients and thermal dispersive effects, are tabulated in numerous publications available to those with skill in the art.

In some aspects of the invention, selection of scatterers for use in various embodiments of the invention is based on adjustable parameters which may include: the wavenumber of radiation to be detected, $k=2\pi/\lambda$, where $\lambda$ is the wavelength of radiation; the mean radius of the scatterers, a; the refractive index of the scatterers, $n_{scatter}$; the refractive index of a medium containing the scatterers, $n_{medium}$, index contrast, $m=n_{scatter}/n_{medium}$, the number density of scatterers, $\rho_N$; and the thickness of the scatter layer, L. These parameters can be found or engineered for a wide range of the electromagnetic spectrum, from X-rays through the microwave region.

In embodiments of the invention, it is useful that materials in scatter layer 103 exhibit low loss of radiation from absorption within the desired range of wavelength detection. Such materials typically will have a small optical loss parameter $\kappa(\lambda)$. The level of tolerable loss depends on the propagation distance and the specific geometry of scatter layer 103. To estimate the electromagnetic radiation intensity loss in a bulk material due to absorption in a material, an exponential function is used: $I(z)=I_o \text{Exp}[-4\pi\kappa'z/\lambda]$, with $I_o$ representing the initial intensity, I(z) representing the residual intensity at depth z, and $\kappa'$, representing the effective loss parameter that depends on the relative fraction of absorbing scatterer particles in the bulk material. For light scattering from small scatterer particles, particularly in the optical resonance regime, the absorption can be greatly enhanced due to the electromagnetic radiation increasing its interaction cross section with the particle, which increases $\kappa'$, but the exponential absorption formula still provides a rule-of-thumb to approximate the loss.

In some embodiments of the invention, scatterers have a size of the same order of magnitude as the dimension of the center wavelength of the wavelength range of radiation to be detected. As a useful rule of thumb, if the longest wavelength of the radiation to be detected is $\lambda_o$, scatterers having a radius a and ranging from $a=\lambda/\pi$ to $a=250\lambda/\pi$ will provide efficient spectral separation. Useful scatter layers for mapping spectrometers of the invention have low absorption and a value of the ratio of the scatterer refractive index to the surrounding medium refractive index, m, that is significantly different from one, for the wavelengths of radiation being scattered. In embodiments of the invention, it is preferred that the scattering medium of scatter layer 103 minimizes radiation absorption while enhancing m.

Generally speaking, speckle patterns will have increased high spatial frequency content for short wavelengths and less high spatial frequency content for long wavelengths. This results in reduced spectral resolution for longer wavelengths. Since the fraction of light passing essentially unscattered through the scatter layer is attenuated exponentially as exp $(-L/l^*)$, where the $l^*$ is the transport mean free path and L is the layer thickness, one method for circumventing a loss of spectral resolution at longer wavelengths is to include, in the scatter layer, scatterers having different sizes such that, for all wavelengths of interest, the ratio of the scatter layer thickness L to the transport mean free path $l^*$ is greater than unity: $L/l^*>1$, ensuring an average of more than one scattering event for all wavelengths. Typically, the transport mean free path $l^*$ reaches a minimum in the Mie scattering regime ka≈0.5-50, although the exact location of the minimum mean free path depends on the ratio $m=n_{scatter}/n_{medium}$ and can be calculated from diffusive transport theory, described further below.

In Mie scattering theory, the size parameter of a scatterer particle is defined as $x=2\pi n_{medium} a/\lambda_0$, where a is the radius of a scatterer particle and $\lambda_0$ is the vacuum wavelength of light to be measured. In a medium containing small scatterer particles of radius a, light of wavelengths $\lambda>4\pi n_{medium} a$ will undergo Rayleigh scattering, corresponding to a particle size parameter of $x<0.5$. In the Rayleigh scattering regime, the scattering cross-section is weak and strongly wavelength-dependent, the transport mean free path $l^*$ is large, and there is significant back-scattering, which does not serve the intended purpose of the scatter layer in the invention. To effectively scatter light of wavelength $\lambda_0$, the scatter layer should contain some scatterer particles with size parameter $x \geq 0.5$. In addition, to ensure light is multiply scattered, the scatter layer thickness L should be thicker than the transport mean free path: $L>l^*$.

When considering the task of optimizing scattering near a single wavelength $\lambda_0$, referred to as a narrowband optimization, the quantity $l^*/a$ expresses the transport mean free path in terms of the scatterer particle radius and may be calculated from photon diffusion theory purely in terms of the scatterer particle volume density $\phi$, index contrast m, and the scatterer particle size parameter x. Photon diffusion theory predicts that the ratio $l^*/a$ achieves some minimum value $l^*_{min}/a$ at some size parameter x in the Mie scattering regime $x_0 \approx 1-50$. Hence, by appropriately choosing the scatterer particle size $a=x_0\lambda_0/(2\pi n_{medium})$ and scatter layer thickness $L>a\times(l^*_{min}/a)$, the wavelength $\lambda_0$ will have transport mean free path $l^*<L$, ensuring multiple scattering near the wavelength corresponding to that size parameter. The total transmission through the scatter layer in the absence of scene element isolators or a reflective coating is approximately $\tau \propto l^*/L$; hence, the scatter layer thickness is practically limited by the intensity of the source and the sensitivity of the detector. For typical applications, the scatter layer thickness should be less than 1000 $l^*$ to ensure adequate transmission of light through the scatter layer to the detector.

When considering the task of optimizing scattering for all wavelengths $\lambda_0<\lambda<\lambda_1$, referred to here as a broadband optimization, it is assumed that refractive index is approximately constant for the wavelengths where spectral reconstruction is required. By way of example only, such a wavelength range could span the visible spectrum (~400-800 nm). For very large size parameters x>>1, photon diffusion theory predicts that the ratio $l^*/a$ is bounded from above by some maximum value $l^*_{max}/a$; hence, by appropriately choosing the scatterer particle size a and scatter layer thickness L, every wavelength $\lambda<\lambda_1$ will have a mean free path $l^*<l^*_{max}<L$, ensuring multiple scattering of all wavelengths of interest within the scatter layer. Given the particle volume density $\phi$, longest vacuum wavelength to be measured $\lambda_1$, and the index contrast m, the smallest size parameter $x_{min}$ that satisfies the requirement $l^*/a<l^*_{max}/a$ can be determined, and typically, $x_{min} \approx 1$. For practical index contrasts, m, scatterers with size parameters smaller than $x_{min}$ will produce Rayleigh scattering, which may have undesirable levels of backscattering. Larger scatterers will lead to Mie scattering and can exhibit significantly more forward scattering and, therefore, transmitted light. From this minimum size parameter $x_{min}$, the minimum required scatterer size $a=x_{min}\lambda_1/(2\pi n_{medium})$ can be calculated. Scatterer particles with size parameters larger than $x_{min}$ may be used if desired, but this will require the scatter layer to be made thicker to accommodate their larger size. For a chosen scatterer size, the thickness of the scatter layer required for multiple scattering at all wavelengths $\lambda_0<\lambda<\lambda_1$ can be calculated as $L>a\times(l^*_{max}/a)$. The scatter layer should be thin enough, less than 1000 $l^*$ in typical applications, to ensure adequate transmission of light to the detector through the scatter layer. Some representative values of the minimum scatterer sizes and scatter layer thicknesses as calculated from photon diffusion theory are listed in Table 2 and may serve as a rule-of-thumb to provide the correct particle size and scatter layer thickness, given the refractive index contrast m and particle volume density $\phi$.

TABLE 2

Optimal scatterer size and minimum scatter layer thickness to produce multiple scattering, as estimated from Mie scattering theory and photon diffusion theory, in terms of the refractive index contrast m and scatterer volume density $\phi$. For the narrowband optimization, $\lambda_0$ is the central wavelength of interest. For the broadband optimization, $\lambda_1$ is the longest wavelength of interest.

| Index Contrast m | Optimal Scatterer Size a (narrowband) | Optimal Scatterer Size a (broadband) | Minimum Scatter Layer Thickness L (narrowband) | Minimum Scatter Layer Thickness L (broadband) |
| --- | --- | --- | --- | --- |
| 1.2 | 20 $\lambda_0/2\pi n_{medium}$ | 6.4 $\lambda_1/2\pi n_{medium}$ | 3.9 a/$\phi$ | 6.1 a/$\phi$ |
| 1.4 | 9.4 $\lambda_0/2\pi n_{medium}$ | 2.1 $\lambda_1/2\pi n_{medium}$ | 1.5 a/$\phi$ | 3.1 a/$\phi$ |
| 1.6 | 4.0 $\lambda_0/2\pi n_{medium}$ | 1.6 $\lambda_1/2\pi n_{medium}$ | 0.87 a/$\phi$ | 2.4 a/$\phi$ |
| 1.8 | 3.6 $\lambda_0/2\pi n_{medium}$ | 1.2 $\lambda_1/2\pi n_{medium}$ | 0.59 a/$\phi$ | 2.0 a/$\phi$ |
| 2.0 | 2.7 $\lambda_0/2\pi n_{medium}$ | 1.1 $\lambda_1/2\pi n_{medium}$ | 0.45 a/$\phi$ | 2.0 a/$\phi$ |
| 2.2 | 2.5 $\lambda_0/2\pi n_{medium}$ | 1.0 $\lambda_1/2\pi n_{medium}$ | 0.38 a/$\phi$ | 1.7 a/$\phi$ |

TABLE 2-continued

Optimal scatterer size and minimum scatter layer thickness to produce multiple scattering, as estimated from Mie scattering theory and photon diffusion theory, in terms of the refractive index contrast m and scatterer volume density $\phi$. For the narrowband optimization, $\lambda_0$ is the central wavelength of interest. For the broadband optimization, $\lambda_1$ is the longest wavelength of interest.

| Index Contrast m | Optimal Scatterer Size a (narrowband) | Optimal Scatterer Size a (broadband) | Minimum Scatter Layer Thickness L (narrowband) | Minimum Scatter Layer Thickness L (broadband) |
|---|---|---|---|---|
| 2.6 | 1.6 $\lambda_0/2\pi n_{medium}$ | 0.93 $\lambda_1/2\pi n_{medium}$ | 0.28 a/$\phi$ | 1.6 a/$\phi$ |
| 3.0 | 1.0 $\lambda_0/2\pi n_{medium}$ | 0.88 $\lambda_1/2\pi n_{medium}$ | 0.22 a/$\phi$ | 1.4 a/$\phi$ |
| 3.6 | 0.8 $\lambda_0/2\pi n_{medium}$ | 0.77 $\lambda_1/2\pi n_{medium}$ | 0.15 a/$\phi$ | 1.4 a/$\phi$ |
| 4.0 | 0.8 $\lambda_0/2\pi n_{medium}$ | 0.71 $\lambda_1/2\pi n_{medium}$ | 0.13 a/$\phi$ | 1.3 a/$\phi$ |

In practice, a thicker scatter layer than those suggested here may be used if it is desired to create speckle patterns with greater wavelength-sensitivity and thus greater spectral and/or polarization separation. In the absence of scene element isolators or a reflective coating, the scatter layer transmission $\tau$ is inversely proportional to the product $\phi L$, so that a very thin scatter layer that is densely populated by scatterers can have a similar transmission to a thick one that is sparsely populated by scatterers. However, since the predicted spectral resolving power is roughly proportional to $L^2/\lambda 1^* \approx L/\lambda\tau$, a thicker, sparsely populated scatter layer is predicted to yield greater spectral resolving power than a thinner one with the same transmission $\tau$. The transmission can be enhanced by including scene element isolators or a reflective coating at the incident surface. Additionally, multiple different scatterer particle sizes or a distribution of particle sizes may be used within the scatter layer to tailor its wavelength-sensitivity across the electromagnetic spectrum.

By way of example only, a scatter layer that efficiently scatters both visible wavelengths (400 nm-800 nm) and infrared wavelengths (900 nm-1,800 nm) may be constructed by embedding within a 30 μm layer of PMMA, small spherical $TiO_2$ scatterers having average radii of 200 nm, among larger spherical scatterers having average radii of 1.1 μm. The larger scatterers will efficiently scatter radiation of infrared wavelengths, while scattering at shorter wavelengths is enhanced by the presence of the smaller scatterers, which scatter light most efficiently near 600 nm and interact minimally with radiation in the infrared band. Another exemplary scatter layer comprises particles having a size distribution selected to achieve sufficient spectral separation or to reduce the effects of fluctuations in scattering efficiency due to Mie resonances.

The criterion x>0.5 and x<500 is a useful starting point by which to determine the optimal size of scatterer particles for a given spectrometer embodiment and provides sufficient spectral separation for scatter layer thicknesses determined using the equations above. However, even at x≈1, backscatter can still occur, reducing the radiative throughput of the scatter layer.

Other parameter regimes, known to those with skill in the art, provide useful additional information for optimizing scatterer size, refractive index, scatter layer thickness, and particle loading). In the regime of multiple scattering of an incident wave by a random medium (e.g., scatter layer 103 in embodiments of the invention), a rigorous analytical description of the scattering process in terms of the wave equation is difficult and is typically limited to variations in the medium on scales much larger than the wavelength. Significant progress in the study of multiple scattering in strongly turbid media has been made by describing wave propagation in terms of diffusive energy transport, rather than dealing with the wave equation directly (Ishimaru (1978), *Wave Propagation and Scattering in Random Media*, Academic Press, San Diego, pp. 148-188). In short, the propagation is modeled as a random walk of light intensity (r) characterized by a transport mean free path, l*. The interference between contributions of many random walks through the sample gives rise to the fluctuations in intensity produced at an observation screen, resulting in a speckle pattern on a detector array, which is produced by the given incident wavelength. Several analytical tools, including correlation functions in particular, can provide insight into the resolution and radiative throughput attainable from a particular set of macroscopic and physical parameters that describe the scatter layer, such as thickness, optical constants of constituents, and the number density and radius or diameter of scatterers within the layer.

In some embodiments of the invention, it is advantageous to use a macroscopic diffusive light transport theory to guide the design of embodiments of the invention for use with particular wavelength ranges, spectral resolutions, and radiative throughput characteristics that match the requirements of specific applications. The central object of interest for determining the properties of the speckle pattern is the transmitted intensity-intensity cumulant correlation function, $$C(r,r';\Delta v) = \langle I_v(r)I_{v+\Delta v}(r') \rangle - \langle I_v(r) \rangle \langle I_v(r) \rangle \langle I_{v+\Delta v}(r') \rangle \quad \text{(Equation 1)},$$

where the angular brackets, "$\langle \ \rangle$", denote an ensemble average and the intensity I is evaluated in a plane in the far-field. This function describes the correlation between speckle patterns produced by transmission through the sample at the positions r, r,' and frequency difference $\Delta v$. For $\Delta v=0$, the decay of the resulting autocorrelation function with |r-r'| gives the typical size of a speckle, whereas for r=r', the decay of the resulting spectrally-lagged correlation function describes the sensitivity of the speckle pattern to a change in wavelength.

Assuming monochromatic light of vacuum wavelength $\lambda_0=2\pi/k_0$ is incident on a scatter layer of thickness L comprising spherical scatterers of refractive index $n_{scatter}$ and radius a embedded within a medium of refractive index $n_{medium}$, the size parameter is denoted as $x=ka=n_{medium}k_0a$ and index contrast $m=n_{scatter}/n_{medium}$. If absorption can be neglected (elastic scattering), which is the case for the majority of high-quality optical materials that would be useful as scatterers with embodiments of the invention, and assuming that there are no long-range intensity correlations, a simple analytic prediction is found for the correlation function in the far-field as a function of frequency lag δν, which has a half-width of $$\delta\nu \approx 1.46\, D/L^2 \quad \text{(Equation 2)}$$

where $D=\upsilon l^*/3$ is the diffusion coefficient for the random walks in three dimensions and $\upsilon$ is the effective speed of energy transport through the medium (Genack and Drake, Europhysics Letters (1990) 11:331-336). This correlation half-width δν describes the change in frequency necessary to cause a significant change in the observed speckle pattern, and is related to the spectral resolving power $$\frac{\lambda}{d\lambda} = \frac{\nu}{|\delta\nu|}.$$

The spectral resolution is the reciprocal of the spectral resolving power. If the spherical scatterers have sizes on the order of the wavelength (x~1), Mie resonances may greatly reduce the effective speed of energy transport through the medium, heuristically estimated by $$\frac{\upsilon}{c} = (\phi(W(x)-1)+1)^{-1} \quad \text{(Equation 3)}$$

(van Albada et al., Physical Review Letters (1991) 66:3132-3135), where φ is the volume density of scatterers and $c=c_0/n_{medium}$ is the speed of light in the scatter layer. The quantity $W(x)$ is the time-averaged electromagnetic energy contained within the (assumed) spherical scatterer, relative to the electromagnetic energy contained in a sphere of scatter layer material of the same size, due to an incident plane wave. This quantity is calculated from Mie theory by the method of Bott et al., (Bott and Zdunknowski, J. Opt. Soc. Am. A (1987) 4:1361-1365) and quantifies the strength of the Mie resonance. The mean free path, $l^*$, for elastic scattering in the sample is given by $$l^* = (\rho_N C_{sca})^{-1} = \frac{4}{3}\frac{a}{\phi Q_{sca}}, \quad \text{(Equation 4)}$$

where $\rho_N=\phi/(4\pi a^3/3)$ is the number density of scatterers, and $C_{sca}$, $Q_{sca}$ are the scattering cross section and efficiency for an individual scatterer, calculated from Mie theory. However, the transport mean free path is given by $$l^*_{trans} = l^*(1-g) \quad \text{(Equation 5)},$$

where $g=\langle\cos\theta\rangle$ is the asymmetry parameter for the scattering pattern of a single scatterer. In the Rayleigh scattering regime, $g\approx 0$ (equal forward and backward scattering), while in the Mie scattering regime $0<g<1$ indicating preferential forward scattering. This transport mean free path describes scattering by clusters of individual particles acting as a single, effectively isotropic scatterer. As the volume density φ increases, inter-particle positional correlations become more significant, requiring a correction to the calculation of scattering cross-section by including the hard-sphere structure factor given by the Percus-Yevick approximation. This correction is not included here, as it is not necessary to achieve a useful approximation to the spectral resolving power, but it predicts (for a given volume density) a larger value for $l^*_{trans}$ than that calculated here. The spectral resolution of mapping spectrometer 100 is determined by the wavelength shift required to cause a significant change in the far-field speckle pattern, which is quantified by the intensity correlation half-width δν. A dimensionless estimate for the spectral resolution is hence found by using the aforementioned relations in Equation 2, which yields, $$d\lambda/\lambda = \delta\nu/\nu \approx 3.06\left(\frac{\nu}{c}\right)\frac{kl^*}{(kL)^2} \approx \quad \text{(Equation 6)}$$
$$\frac{4.08}{(kL)^2}\frac{1}{\phi(W(x)-1)}\frac{x}{\phi Q_{sca}(x)(1-g(x))},$$

where $k=2\pi n_{medium}/\lambda_0$ is the wavenumber in the ambient medium. The spectral resolution is optimized in the range of size parameters corresponding to the first few Mie resonances. For smaller size parameters, Rayleigh scattering has far too small a scattering cross-section to give rise to effective diffusion, while for larger size parameters, increased forward scattering and higher order Mie resonances cause an increase of dλ/λ, with x (i.e., lower spectral resolving power) superposed with large fluctuations whose magnitude increases with index contrast m. As m decreases to unity, which corresponds to optically "soft" spheres, the scattering length increases rapidly. A larger index contrast yields a larger spectral resolving power near x≈1 to x≈2, but at the cost of increasing the magnitude of fluctuations due to Mie resonances and potentially reducing the spectral range over which this resolution is consistently attained.

As incident light is scattered by scatterer particles, there is an initial exponential decrease of the unscattered intensity with $L/l^*$. In the multiple scattering regime ($L>l^*$), the scattered light propagates diffusively, leading to a total transmission τ through the medium $$\tau \propto \frac{kl^*}{kL} \quad \text{(Equation 7)}$$

(Ishimaru, 1978), which exhibits the same linear dependence on $kl^*$ as dλ/λ, but only a linear inverse dependence on kL. Given a certain requirement on the transmitted intensity, this requirement can be maintained while increasing the spectral resolving power by increasing kL and proportionately increasing $kl^*$. This may be achieved, for example, by decreasing φ and increasing L, since φ and L can be controlled independently during fabrication. That is, increasing the thickness of the scatter layer and decreasing the scatterer particle loading density can increase total transmission τ without reducing spectral resolving power. These calculations do not take into account the use of reflective surfaces to confine the light within a single scene element 203, which serves to increase both total transmission and spectral resolving power.

FIG. 8 shows exemplary scatterers, approximate scatterer dimensions, scatter layer media and approximate dimensions, and detector arrays for detecting radiation in selected exemplary ranges of the electromagnetic spectrum, and calculated spectral resolving power across the band using a diffusive theory of light. Resolving power is a dimensionless value. All other units are shown in the table. Average scatterer radii in the range of 0.5≤ka≤500 are particularly useful in some embodiments of the invention. Ultimately, optimization of the scatter layer depends on the design goals, which may be, for example, to achieve maximum spectral resolving power over a small wavelength range, or to achieve constant spectral resolving power over a wide wavelength range, or to minimize scatter layer thickness, to name only a few possibilities. The diffusive transport theory described previously can be used without undue experimentation, by one with skill in the art, to optimize the scattering layer for these and other design goals.

Exemplary scatterers such as textured surfaces, particles (e.g., nanoparticles and microparticles), gaseous inclusions, voids, sintered particles, inhomogeneous mixtures of compounds with contrasting refractive indices, radiation-damaged glasses and crystals, and frit glass may also be useful for scattering spectral and/or polarization components of radiation, and thus for use in scatter layer 103. Additional materials that may be useful as scatterers, particles, and agglomerations include fiber meshes, weaves, and mats, such as thin fiberglass layers, or ceramic or metal foams, polymers including PMMA and other acrylics, polyamides, nylon, polyimides, polyurethanes, vinyl chlorides including PVCs, polyvinyls, polycarbonates, polyesters including PET, cyclic olefin copolymers, silicones, fluoropolymers, polystyrenes, silanes, polymethylpentene, PMDS, optical epoxies, stilbene, cellulose acetate, polypropylene, and others, which are well known to those in the art. Numerous polymer microspheres with a variety of size tolerances are also available commercially (Bangs Laboratories, Inc. Fishers, Ind., USA; Cospheric LLC, Santa Barbara, Calif., USA).

Exemplary methods and technologies that may be useful for preparing scatter layers include technologies developed for rear-projection screens like CRT monitors and disclosed in U.S. Pat. Nos. 1,176,746, 2,474,061, and 4,053,208. U.S. Pat. No. 5,264,197 discloses exemplary methods for preparing sol-gel glass with controlled porosity, which can function as a scatter layer. U.S. Pat. No. 5,534,386, discloses methods for producing a homogenizer from a holographic diffuser. Additional published methods are available for (1) producing strain-induced birefringence that results in a material that can function as a scatter layer for x-rays (Pollanen et al., J Non-Crystalline Solids (2008) 354:4668-4674), (2) predicting the x-ray/VUV scattering performance of most atomic species (Henke et al., Atomic Data and Nuclear Data Tables (1993) 54(2):181-342), and (3) using sol-gel processes to produce porous scattering layers for a wide variety of materials, including $CaF_2$ which can scatter UV light (Fujihara et al., J Sol-Gel Sci Technol (2002) 24:147-154].

Sintered microparticles and nanoparticles are examples of mechanically robust radiation scatterers. Microparticles and nanoparticles can be prepared, for example, by mechanically milling bulk materials and performing a size selection step, such as sieving or field-flow fractionation. Other means of producing microparticles and nanoparticles include, by way of example only, spray pyrolysis, laser ablation, thermal decomposition in plasma, sol-gel processing, solution combustion decomposition, vapor deposition, and synthesis from chemical precursors. The intermediate stage of sintering results in a porous medium that is connected and can be mechanically robust.

Some scatter layers, such as for example, porous metal and metal-fluoride films that are effective in the UV, EUV, and VUV spectral ranges (e.g., $MgF_2$) may be made by deposition onto an optical substrate at a glancing angle, which results in a highly porous film due to self-shadowing effects (Robbie et al., J. Vac. Sci. Technol. A (1995) 13(3): 1032-1035). $MgF_2$ can also be prepared in other tunable and laboratory controllable ways and then sintered by any of a variety of methods, such as for example, methods described in Nandiyanto et al., Langmuir (2010) 26(14): 12260-12266 or Shi et al., JMMCE (2004) 3(2): 105-108. Methods for producing particle inclusions and binary-phase scattering layers include precipitation or grain growth of a species from a solution or melt at elevated temperature and co-sintering two powders. Sintered $TiO_2$ microparticles for use in scattering layers are commercially available in a variety of size ranges and can be thermally sintered with a hot press, chemically sintered, and sintered by microwave. ZnS powders for use in preparing scatter layers for spectrometer embodiments that detect and image radiation in the SWIR and MWIR ranges can be produced and sintered in a controlled manner (Kim et al., J Mater Sci (1997) 32:5101-5106; Vacassy et al., J Am Ceram Soc (1998) 81(10):2699-2705). ZnS and ZnSe powders for use in scatter layers when detecting and imaging radiation in the MWIR and LWIR may be prepared from hot-pressed particle films (Harris, SPIE Proc. 6545:Art.ID 654502). Still other methods of producing ZnSe microspheres include hydrothermal synthesis routes (Duan et al., Trans Nonferrous Met Soc China (2014) 24:2588-2597). Additional methods for producing scatter layer films include deposition of the scattering material at high temperature onto an optical substrate with a significantly different coefficient of thermal expansion, resulting in cracking as the substrate cools after deposition. Additional processing parameters and considerations for single-phase sintering are available to those with skill in the art.

Exemplary methods for validating and quantifying scatterer properties prior to incorporation into a device include static light scattering (such as angle-resolved scattering), dynamic light scattering if the scatterers are readily suspended in a fluid, and diffusing-wave spectroscopy. Morphological characterization, by techniques such as scanning electron microscopy (SEM), profilometry, or atomic force microscopy, is also useful. The results of these measurements will provide validation that the structures produced are of the requisite dimensions and optical properties prior to integration and evaluation with a particular spectrometer embodiment. Means of characterizing scattering layers include cross-sectional scanning electron microscopy (SEM), total integrated scattering (TIS) light measurements and angle-resolved scattering (ARS) light techniques.

The physics and engineering principles of mapping spectrometers of the invention are not limited to a specific band of electromagnetic radiation and are invariant across the electromagnetic spectrum. Therefore, the spectral range within which a given mapping spectrometer of the invention is useful is limited only by the range of detector array sensitivity, and the spectral resolving power is limited only by the number of pixels on the detector that comprise the speckle patterns (though additional techniques can be used to increase the spectral resolving power, e.g., dithering the position of the scattering plane).

Mapping spectrometers of the invention may comprise any type of detector array that can detect electromagnetic radiation and is amenable to the chosen format of the spectrometer. In some embodiments of the invention, detector arrays useful with mapping spectrometers of the invention are commercially available and as such, have pre-determined sensitivities to radiation in selected regions of the electromagnetic spectrum. The type of detector array useful in a given spectrometer embodiment will depend on the specific application of the mapping spectrometer. Detector array choice may be based on the range of wavelengths of the radiation to be detected, the type of scatter layer, dark current, readout noise, integrated microlenses, and front/ back illumination. By way of example only, back-thinned silicon CCDs are useful for detecting electromagnetic radiation within the region of the spectrum from 150 nm to 400 nm. Utilization of the full spectral range of such a CCD is within the scope of the invention. Additional examples of detector array 104 useful in embodiments of the invention include CCD and CMOS arrays configured for detection of electromagnetic radiation having wavelengths from 300 to 1,100 nm and focal plane arrays configured for detection of electromagnetic radiation having wavelengths from 500 nm to 20,000 nm. Exemplary focal plane arrays include InGaAs focal plane arrays for detecting electromagnetic radiation having wavelengths from 500 nm to 2,000 nm, InSb, CdTe, PtSi, and PbSe focal plane arrays for detecting electromagnetic radiation having wavelengths from 3 µm-5 µm, and HgCdTe and microbolometer focal plane arrays for detecting electromagnetic radiation having wavelengths from 3 µm-10 µm or from 8 µm-20 µm. Still other exemplary detectors include microbolometer arrays for thermal infrared and LWIR radiation detection (3 µm-20 µm). Additional detector materials may include, by way of example only, silicon for use with visible light imaging (400 nm-800 nm), InGaAs and PbS for use with SWIR detection (0.7 µm-3 µm), and InSb, PbSe, PtSi, and HgCdTe for use with MWIR detection (3 µm-5 µm). Detector arrays for use in embodiments of the invention may also be configured for detecting and imaging radiation having other wavelengths within the electromagnetic spectrum, such as for example wavelengths in the EUV/VUV, very long wave infrared, millimeter wave, microwave, and radio-frequency regions of the electromagnetic spectrum. Additional useful detector arrays include organic photodetector arrays, Golay cell arrays, rectenna arrays, and antenna arrays. In some embodiments of the invention detector arrays comprise a phosphor or scintillator coating that converts the wavelength of electromagnetic radiation to a different wavelength. One example of an x-ray and gamma phosphor is the rare-earth compound $Gd_2O_2S$: Pr. Examples of scintillator materials include alkali halide and transition metal halide crystals, such as CsI and $LaBr_3$, respectively. Embodiments of the invention using detectors of this type provide spectral resolution capability in the x-ray and gamma region of the electromagnetic spectrum.

In some embodiments, a mapping spectrometer is sensitive to both spectral components of and the polarization of incident radiation 105, enabling the acquisition of data about both spectral components and the polarization state of radiation. The unique spectral speckle pattern produced by the scatter layer is often polarization-dependent. To measure the polarization state, it is necessary to calibrate spectrometers with polarized light. Information regarding the polarization state of incident radiation may be useful in remote sensing applications for determining the particle size of remote aerosols, detecting the presence of metals or specific mineral species, or for determining the orientation of mechanically stressed or anisotropic materials. In other embodiments, it is preferred that a mapping spectrometer not be sensitive to polarization. In these embodiments, a mapping spectrometer may comprise a depolarizer positioned between incident radiation 105 and aperture array 101. In another embodiment a polarization filter is present between aperture array 101 and scatter layer 103 and a second, orthogonal polarization filter, for filtering unscattered radiation, is present between scatter layer 103 and detector array 104.

As described earlier, the set of detector array pixels 107 that are allocated to and may be illuminated by scattered spectral components of radiation that has passed through a single aperture 102 is defined as a scene element 203. For embodiments of the invention in which a spectrometer comprises a concentrator array 200 with each concentrator in register with a single aperture, the number of scene elements on detector array 104 corresponds to the number of concentrator/aperture combinations. For spatial and spectral resolution, a detector array 104 having M×N pixels can be subdivided in any of a variety of ways to define individual scene elements 203. For explanatory purposes, consider detector array 104 shown in FIG. 2. Detector array 104 comprises 25 scene elements 203 in a simple 5×5 array configuration, with each scene element representing a grouping of pixels that is defined by scene element isolators 204. In FIG. 2, for simplicity of viewing, not all scene elements 203 are outlined on detector array 104, but will be apparent based on the arrangement of those representative scene elements depicted and scene element isolators 204 shown in the exploded view. Each scene element represents a single data point available for spatial resolution. In this example, each scene element 203 (pixel grouping) comprises a region of the detector having 56 pixels (an 8×7 pixel grouping). Thus, detector array 104 has a 40 pixel (M) by 35 pixel (N) configuration for a total of 1,400 pixels 107 on the array. The mapping spectrometer spatial resolution is $$\frac{M}{8} \times \frac{N}{7} = \frac{40}{8} \times \frac{35}{7} = 25.$$

That is, 25 scene elements are available for spatial resolution. However, each scene element comprises 56 pixels, and thus 56 pixels are available for resolving the spectral content within each scene element.

Figure 9:
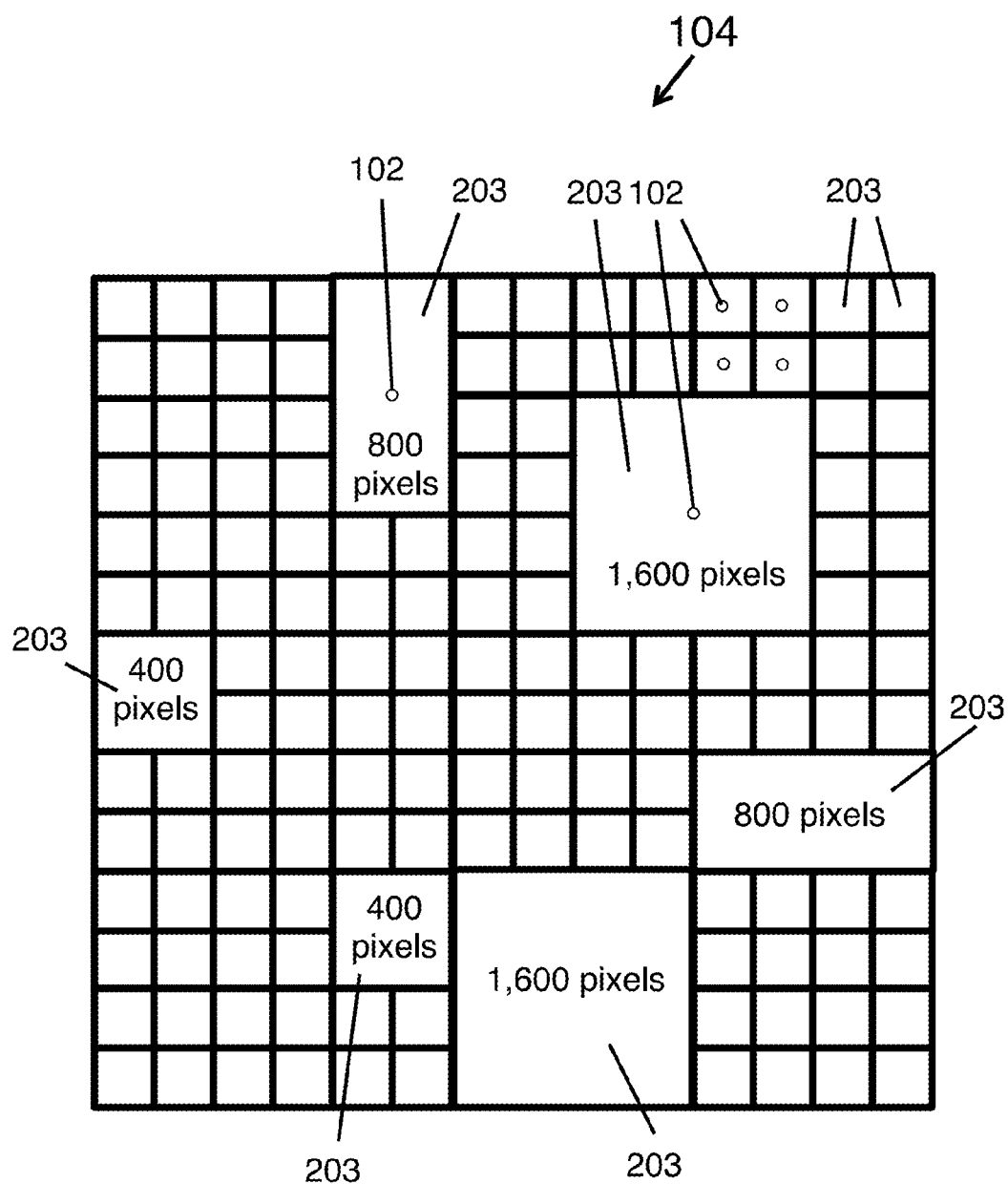
FIG. 9 is an exemplary representation of scene elements on a detector array, in which scene elements differ in spacing, size, and shape.

As described above, FIG. 2 shows an exemplary scene element 203 grid with uniform scene element spacing. However, in some embodiments, scene elements are not uniform in spacing, size, or shape. FIG. 9 is an exemplary representation of scene elements on a detector array, in which scene elements differ in spacing, size, and shape. Each square or rectangle represents a scene element 203. Small circles shown within some scene elements represent apertures 102. For simplicity of viewing, only a subset of apertures 102 and scene elements 203 are labeled. If present, a single concentrator is in register with a single aperture and hence a single scene element. The figure depicts an additional exemplary scene element 203 grid for an exemplary detector array 104. Each small square represents a 10 pixel by 10-pixel scene element 203 (100 pixels per scene element). Therefore, the detector array 104 shown in FIG. 9 has 19,600 pixels. Each scene element represented by a small square corresponds to 100 pixels on detector array 104 that may be used for spectral resolution and corresponds to a single data point for spatial resolution. Larger scene elements are represented by larger boxes (squares or rectangles here) and comprise a larger number of pixels than the small, 100-pixel squares. In the figure, the larger scene elements are labeled with the corresponding number of pixels on the detector array. Large scene elements also represent a single data point for spatial resolution, and while enhancing spectral resolution (the ability to separate and identify spectral components 106), do so at the expense of spatial resolution and spatial information. Small circles shown in some scene elements represent apertures 102 through which radiation passes to a scatter layer and thence to the scene element pixels on the detector array. Each scene element 203 is associated with a single aperture 102 and represents the group of pixels on detector array 104 that may be illuminated by radiation passing through the associated aperture.

To ensure that the speckle pattern is distributed over the scene element pixels, and not incident on a single pixel, the far-field speckle grains are designed to have dimensions similar to those of the pixels. Since the size of fluctuations in the transmitted intensity field (i.e., approximate speckle grain dimension) within the scatter layer has size of order of the transport mean free path l*, speckle grains produced in the far field (i.e., at the detector) by light of wavelength λ have an angular extent of approximately θ≈λ/l*. To unambiguously detect the smallest speckle grains produced by the scatter layer, in some embodiments the detector may be positioned at a distance from the scatter layer such that over the range Λ of wavelengths being detected, each detector pixel occupies an angular extent≈$\min_{\lambda \in \Lambda} \lambda/l^*$. Similarly, to unambiguously detect the largest speckle grains produced, in some embodiments the portion of the detector assigned to a particular scene element may include a sufficient number of pixels so as to detect the largest speckle grains produced, so that the set of detector pixels assigned to a particular scene element occupies an angular extent≈$\max_{\lambda \in \Lambda} \lambda/l^*$. One skilled in the art will appreciate the requirements for ensuring the speckle pattern is distributed across the pixels for maximum pixel utilization.

Figure 10:
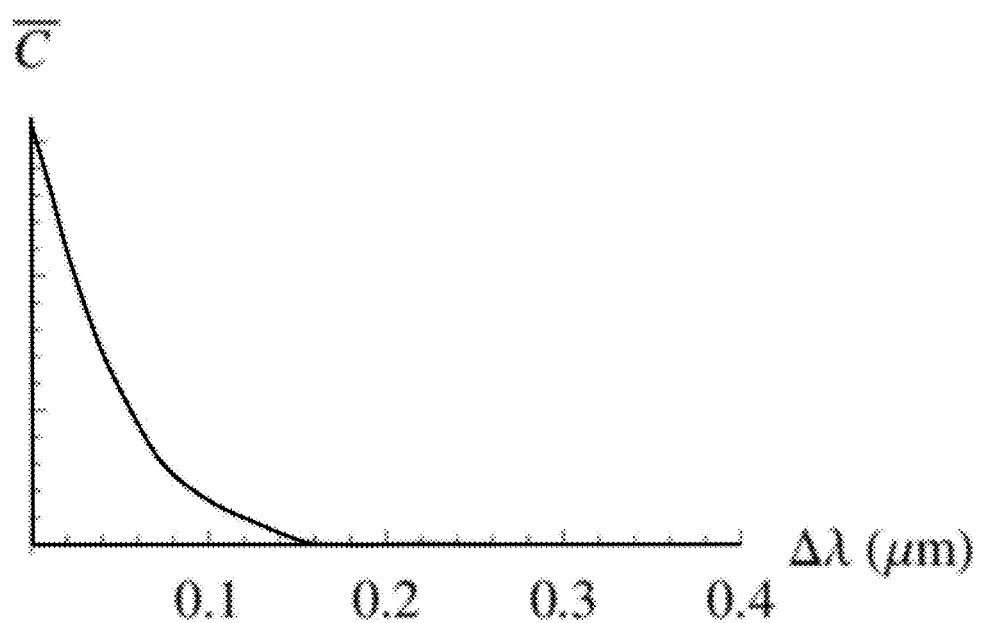
FIG. 10 shows a correlation plot for a set of speckle patterns. In this figure, the half-width of the correlation peak $\Delta\lambda_{1/2}$ is ~0.04 μm.

Theoretically, for radiation that is maximally scattered by scatter layer 103, each pixel 107 may provide spectral information regarding a single wavelength of radiation. In this situation, scene elements comprising 100 pixels on a detector array may provide spectral information for 100 spectral components of radiation. However, due to the random nature of the speckle patterns, spectral components of two different wavelengths may inadvertently produce speckle patterns that a detector may identify as being similar. Also any source of noise will reduce spectral discrimination. Therefore, using a 100-pixel scene element to provide an over-determined number of spectral bands (i.e., fewer spectral bands than pixels), such as for example 75 spectral bands, will provide improved robustness against noise. Typically, utilization of ~50% to 75% of pixels for spectral resolution provides a useful detector and a robust spectral range. However, higher pixel utilization is technically possible. A more quantitative measure of the spectral discrimination in a scene element is provided by the spectrally-lagged correlation function shown here $$C(\Delta\lambda, x) = \langle I(\lambda,x)I(\lambda+\Delta\lambda,x)\rangle_\lambda / [\langle I(\lambda,x)\rangle_\lambda \langle I(\lambda+\Delta\lambda,x)\rangle_\lambda] - 1 \quad \text{(Equation 8)},$$

where I(λ, x) is the mean-subtracted intensity recorded at detector pixel x for input wavelength λ, Δλ is the spectral lag, and $\langle \ldots \rangle_\lambda$ indicates the average over wavelengths. Essentially, the equation compares the spectral response at a pixel x at a wavelength λ to the same pixel's response at a slightly shifted wavelength λ+Δλ. A response of C(Δλ,x)=−1 indicates that the two signals are identical; C(Δλ,x)=0 indicates no correlation; C(Δλ,x)=−1 indicates that the two signatures are exactly opposite. The spectrally-lagged correlation function thus provides a statistical measure of how a pixel in a scene element changes between two different wavelengths as a function of frequency. By averaging C(Δλ) over all pixels within a scene element, a typical response is shown in FIG. 10. FIG. 10 shows a correlation plot for a set of speckle patterns. In this figure, the half-width of the correlation peak $\Delta\lambda_{1/2}$ is ~0.04 μm. The function has a half-width, $\Delta\lambda_{1/2}$, at which point the spectral signatures are half-correlated. This can be used to estimate how overdetermined the spectral resolution will be. An overdetermined system is one in which there are more measurements than degrees of freedom. In the context of the invention, an overdetermined system is one in which more pixels are present in a scene element than spectral components to be determined. For instance, by choosing spectral bins of size 2 $\Delta\lambda_{1/2}$, the adjacent spectral bins will be de-correlated. By choosing spectral bins of size 3 $\Delta\lambda_{1/2}$, the system will be ~50% overdetermined.

Scene element sizes and shapes of the invention may be adjusted and designed to acquire more or less spatial or spectral information. They may take any of a variety geometrical shapes, such as circles, ellipses, triangles, hexagons, or other shapes and will depend on the application for which the mapping spectrometer is designed. Just as scene elements may vary in size and shape, so may concentrators. Concentrators need not be regularly arranged, uniformly sized, square, or rectangular.

In some embodiments of the invention, a mapping spectrometer comprises scene element isolators. Scene element isolators 204 are configured to prevent scattered components of radiation from illuminating adjacent scene elements on the detector array that are associated with a different aperture. In some embodiments of the invention, scene element isolators comprise a reflective surface. In certain aspects of the invention, scene element isolators are useful for simplifying the computational determination of spectral data acquired from detector array 104 by preventing radiation scattered by the scatter layer from illuminating pixels in an adjacent scene element of the detector array.

In various embodiments of the invention, scene element isolators 204 may be positioned differently with respect to aperture array 101, scatter layer 103, and detector array 104. By way of example, in some aspects of the invention, scene element isolators may be embedded within a scatter layer, as depicted in FIG. 2. In other aspects, scene element isolators may be embedded within and extend below the scatter layer as shown in FIG. 3, or they may be positioned below but not in contact with scatter layer 103. In still other aspects of the invention, scene element isolators may extend below the scatter layer to the surface of the array detector, and in some aspects contact the detector array. Similarly in other aspects of the invention, scene element isolators may contact aperture array 101.

In other embodiments of the invention, a mapping spectrometer does not comprise scene element isolators. In embodiments of mapping spectrometers that lack scene element isolators, radiation destined for one scene element may stray and illuminate pixels in an adjacent scene element of a detector array. This situation can be accounted for during computation of spectral data. Alternatively, scene elements of a detector array may be spatially separated without isolators by increasing the distance between apertures 102 of aperture array 101. The absence of scene element isolators may be desirable in some embodiments of the invention, as isolators may block pixels on a detector array. Ultimately, the dimensions and use of scene element isolators will be determined by the application.

Embodiments of the invention include methods for identifying and analyzing electromagnetic radiation and spectral components of electromagnetic radiation and for producing hyperspectral or spectral images. A mapping spectrometer of the invention may be used for analyzing one or more spectral components of electromagnetic radiation. Methods of the invention utilize various embodiments of the spectrometer of the invention for receiving, electromagnetic radiation through an array of apertures and separating the radiation into spectral components that illuminate pixels on a detector array. In some aspects of the invention, radiation is received, gathered, and concentrated by one or more concentrators prior to passing though the array of apertures. Illumination of pixels on a detector array produces a speckle pattern, and speckle pattern data are used to computationally identify one or more spectral components of incident electromagnetic radiation. In some aspects of the invention, analyzing spectral components of electromagnetic radiation further comprises producing a hyperspectral or spectral image. In additional aspects of the invention, analyzing electromagnetic radiation further comprises identifying the polarization state of the radiation. In further aspects of the invention, analyzing electromagnetic radiation comprises identifying spatial information about the electromagnetic radiation.

Figure 11:
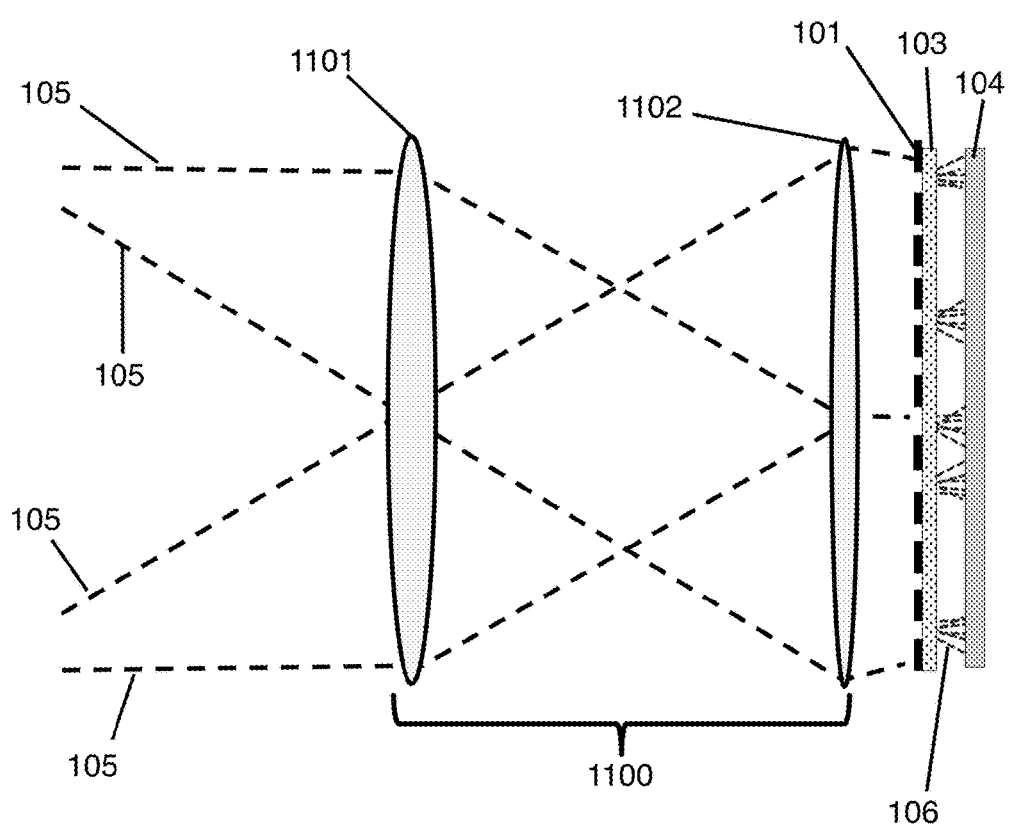
FIG. 11 is a schematic representation of one embodiment of a mapping spectrometer showing exemplary optional imaging optics 1100.
Figure 12:
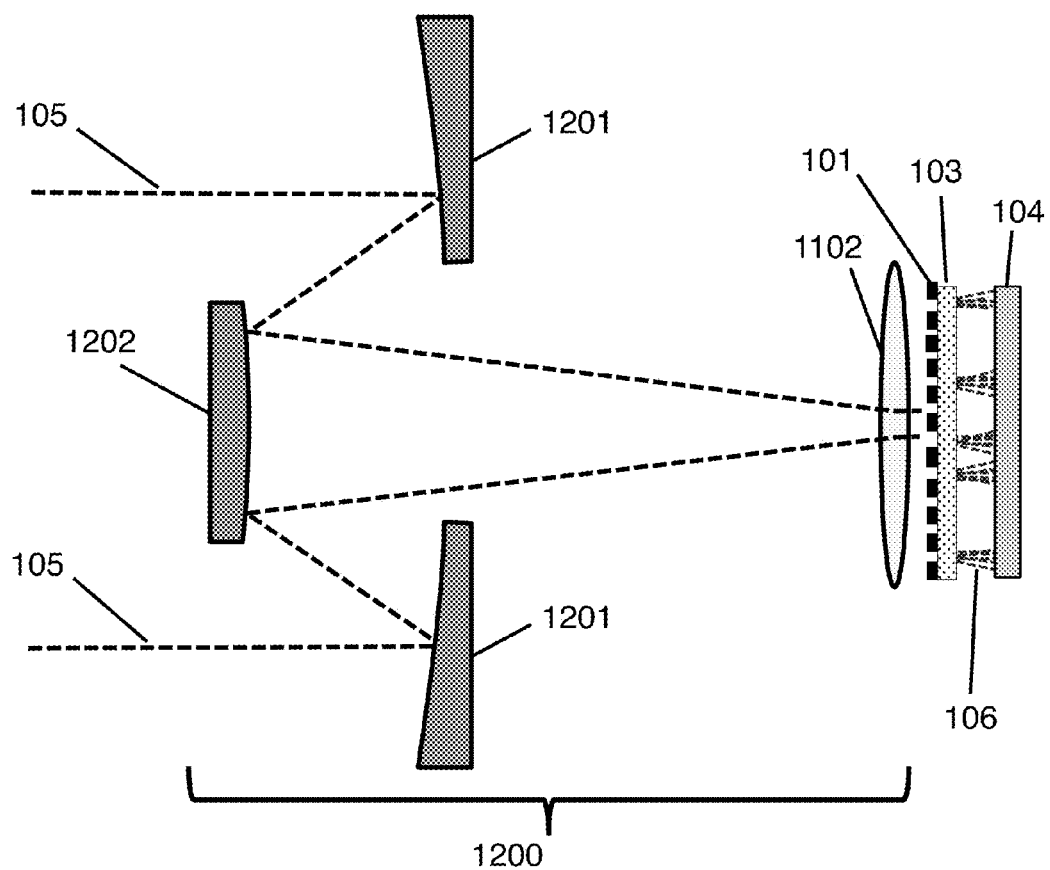
FIG. 12 is a schematic representation of exemplary reflective imaging optics 1200 designed for broadband input with minimal chromatic aberration.

In some aspects of the invention, a mapping spectrometer of the invention may be used with imaging optics for the purpose of forming a spectral or hyperspectral image. Imaging optics direct radiation from an object or a scene to a mapping spectrometer for detecting incident radiation or forming a spectral or hyperspectral image. Imaging optics include optical configurations known to those in the art as a camera objective lens, telescope, periscope, or microscope. In some embodiments of the invention, imaging optics are positioned to form an image of a scene at the plane of the mapping spectrometer. In embodiments of spectrometers not having concentrators 201, the imaging plane of the mapping spectrometer is the first surface of the array of apertures, i.e., the surface at which electromagnetic radiation arrives at the aperture array. In embodiments of spectrometers having concentrator arrays, the imaging plane of the mapping spectrometer is at the entrance to the concentrator array. FIG. 11 is a schematic representation of one embodiment of a mapping spectrometer showing exemplary optional imaging optics 1100. Imaging optics 1100 comprise objective lens 1101 and field lens 1102. Radiation 105 is collected and focused by lens 1101 and field-flattened by lens 1102. Radiation then passes through aperture array 101 and scatter layer 103 and is separated into spectral components 106 for detection by detector array 104. FIG. 12 is a schematic representation of exemplary reflective imaging optics 1200 designed for broadband input with minimal chromatic aberration. Reflective imaging optics 1200 comprise concave annular mirrors 1201, convex mirror 1202, and field lens 1102. Radiation 105 is reflected by mirrors 1201 and 1202 and field-flattened by field lens 1102. Radiation passing through aperture array 101 is scattered by scatter layer 103 and separated into spectral components 106 for detection by detector array 104. It is contemplated that use of a mapping spectrometer of the invention is not limited to any specific form of imaging optics. Furthermore, it is contemplated that any embodiment of a mapping spectrometer of the invention may be used with imaging optics. The nature and form of optional imaging optics for use with a mapping spectrometer is dependent on the desired function of the spectrometer.

Figure 13A:
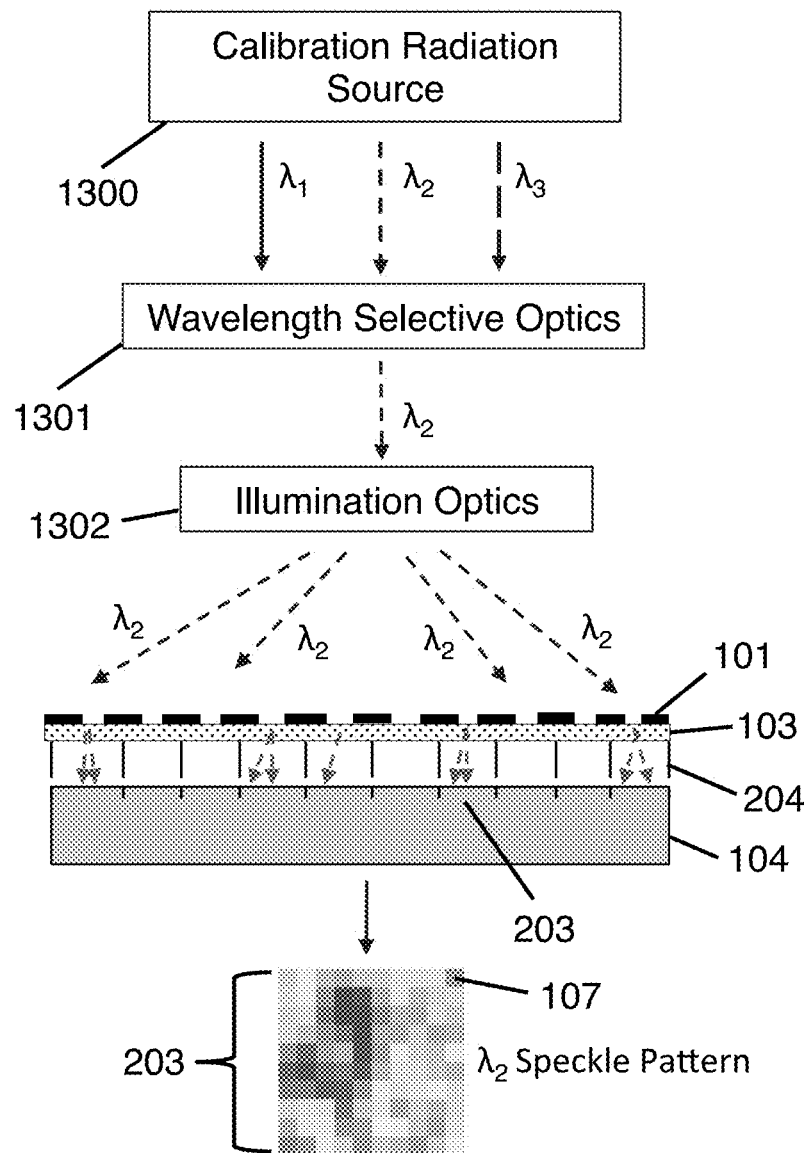
FIG. 13A depicts exemplary methods and hardware useful for producing speckle patterns for calibration from known spectral components that span a wavelength range of interest.

In some embodiments of the invention, analyzing spectral components of radiation further comprises calibrating a mapping spectrometer. FIG. 13A depicts exemplary methods and hardware useful for producing speckle patterns for calibration from known spectral components that span a wavelength range of interest. Exemplary methods and hardware useful for the production of speckle patterns from known spectral components that span a wavelength range of interest $\Lambda$, where $\Lambda=[\lambda_{min}, \lambda_{max}]$ are depicted schematically. Calibration radiation source 1300 provides a spectral basis set, $\phi$, for use in calibration. Exemplary calibration radiation sources 1300 useful for providing the basis set include tunable sources or continuum sources. Commercially available examples include, by way of example only, thermal sources, high-pressure arc lamps, and supercontinuum fibers.

In this example, radiation source 1300 emits radiation having spectral components with wavelengths of $\lambda_1$, $\lambda_2$, and $\lambda_3$. Wavelength selective optics 1301 transmit radiation of a single wavelength, $\lambda_2$, to illumination optics 1302, which ensures full illumination of the mapping spectrometer by the radiation. Radiation then passes through aperture array 101, interacts with scatter layer 103, and illuminates pixels 107 within scene elements 203 on detector array 104, the scene elements being defined by scene element isolators 204. The pattern of pixel illumination in a scene element, for a given wavelength, is the speckle pattern for that wavelength. The illumination optics should direct radiation uniformly over all scene elements 203 and from the same range of incident angles that the spectrometer will be exposed to during operation. In some embodiments, band pass filters in wavelength selective optics 1301 may be used for calibration and in standard operation to ensure that only wavelengths in the range $\Lambda$ are detected. The choice of wavelength selective optics for calibrating a mapping spectrometer depends on the spectral band of interest. Commercially available and useful exemplary optics include filters, diffraction gratings, prisms, acousto-optic modulators, tunable crystal filters, x-ray Bragg filters, or tunable microwave cavities. Additionally, in some aspects of the invention, a polarization filter or depolarizer may be included, between wavelength selective optics 1301 and illumination optics 1302 for instance, to measure the polarization-dependent or depolarized speckle patterns, respectively.

Figure 13B:
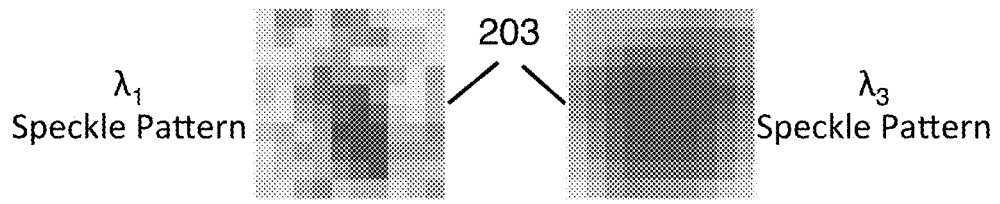
FIG. 13B depicts speckle patterns in a scene element for two different wavelengths of radiation from a calibration source.

Each wavelength of radiation in the range of interest makes a reproducible speckle pattern, on the pixels 107 corresponding to each scene element 203, with a given mapping spectrometer. FIG. 13B depicts speckle patterns in a scene element for two different wavelengths of radiation from a calibration source. Exemplary speckle patterns within a scene element that are produced by radiation having wavelengths $\lambda_1$ and $\lambda_3$ are shown. In the examples shown here, scene element 203 comprises a grouping of 100 pixels in a 10×10 square array. Speckle patterns are measured by detector array 104 as a function of incident wavelength and intensity of radiation and converted to electrical signals for calibration and storage.

For a given scene element, each individual speckle pattern serves as a basis vector for each wavelength of interest. The set, $\phi$, of basis vectors for $\Lambda$ is measured and then used in an algorithm for determining the magnitude of the spectral components of radiation having wavelengths in the range of interest. First a transmission matrix T is measured from the known spectral inputs. If, during operation of the invention, a scene element of the invention is intended to provide a determination of the spectrum with Y spectral bins, then the calibration basis set, $\phi=\{\phi_i\}$, must have a minimum of Y elements, that is, Y spectrally-independent calibration measurements made at a set of wavelengths that span $\Lambda$. Using more than Y spectral calibration measurements will provide an overdetermined set and may be beneficial and preferred. If a scene element with V total pixels and the calibration basis set, $\phi$, has Y spectral bins, the transmission matrix, T, will have dimensions V rows×Y columns. For spectral input $\phi_i$, the measured intensities of the V pixels will be recorded as the $i^{th}$ column in matrix T.

In some embodiments of the invention, the spectral components incident on the scene element are identified computationally, after calibration, using algorithms that employ the calibration measurements in matrix T. Once T has been assembled, determining an unknown spectrum, S, can be undertaken. The intensity vector (of length V), denoted as b, from the pixels within the scene element is measured. One method of determining the vector of spectral components S, for the special case where V=Y, is to use the inverse of the transmission matrix to solve the linear system: $S=T^{-1}b$. This method is straightforward, but may be susceptible to noise. More generally, especially for V≠Y, finding S is a minimization problem, well known in the art of linear algebra and optimization. Several approaches exist for overcoming noise and the need for a square transmission matrix. An effective and simple method is Tikhonov regularization. For regularization parameter α and Tikhonov matrix $_\Gamma=\alpha I$, the spectral components S can be determined as $S=(T'T+_\Gamma'_\Gamma)^{-1}T'b$, where ' represents the transpose operator, and α is chosen to be a small value that provides stability of S in the presence of noise in b.

Additionally, speckle patterns that are assembled into a calibration/scattering matrix, T, can be studied algebraically for desirable properties, such as the matrix condition number cond(T)=$\|T^{-1}\|\cdot\|T\|$ where $\|\,\|$ denotes a matrix norm, such as the Frobenius norm. The condition number may also be expressed as the ratio of the maximum singular value of T to the minimum singular value of T, and is always greater than or equal to 1. The condition number quantifies the sensitivity of the spectral reconstruction S to noise in the measured detector signal b via the matrix equation TS=b. Generally, noise in the detector vector b will be amplified by the factor cond(T) in the spectral reconstruction S. Matrices T with condition number close to unity are desirable for robust spectral reconstruction in the presence of noise.

Also useful are algorithms for determining the spectral components S, which can also provide non-negativity constraints, such as simulated annealing, L1-L1 and mixed L1-L2 methods, constrained least squares, maximum likelihood, and maximum entropy methods. Other options include recursive methods. Initially, the system is solved to determine $S_1$ at low spectral resolution, then a higher spectral resolution solution $S_2$ is determined using the low-resolution solution to initialize the solver, and so on, until the final solution for S, containing Y elements, is determined. All of these techniques may be performed on the real-space (literal detector readout) data or the Fourier domain data, where a fast Fourier transform (FFT) or windowed FFT is performed on the detector data (vector b) prior to solving for S. The frequency domain may provide some sensitivity advantages for broadband spectral reconstruction, where larger speckle grains are typically associated with longer wavelengths and will be more distinct from the smaller speckle grains associated with shorter wavelengths. Modern computational tools, multi-core processors and graphics processing units (GPUs), are capable of performing these calculations at extremely high rates and allow the spectrum to be computed at video rates (>1 Hz). Spectral component identification and spectral or hyperspectral image production may occur repetitively at high frequency, for example at a frequency of between 1 Hz and 100 Hz.

In some embodiments of the invention, a mapping spectrometer further comprises a substrate onto which the spectrometer is affixed. In some aspects of the invention, a substrate comprises an integrated circuit. In additional embodiments of the invention, a mapping spectrometer of the invention further comprises or is in communication with one or more devices or hardware for data analysis, such as a computer, storage device, communication interface, buffer, and/or data or image processors that are configured to perform calibration of spectrometers or to receive, store, and/or process measurements that result from radiation illuminating pixels on a detector array. Mapping spectrometers may also comprise computer software for calibration and/or for executing algorithms for determination and analysis of spectral and/or polarization components. Calibration, spectral component determination, implementing an algorithm, and analysis of spectral components may be implemented on tangible computer-readable medium comprising computer-readable code that, when executed by a computer, causes the computer to perform one or more operations. A processor or processors can be used in performance of the operations driven by the tangible, computer-readable media. Tangible computer-readable media may be, for example, a CD-ROM, a DVD-ROM, a flash drive, a hard drive, a non-volatile memory device, or any other physical storage device. Alternatively, the processor or processors can perform those operations under hardware control, or under a combination of hardware and software control. In some embodiments of the invention, data resulting from measurements from a detector array may be transferred to a storage device for processing at a later time or transferred to another computer system on demand via a communication interface.

Figure 14:
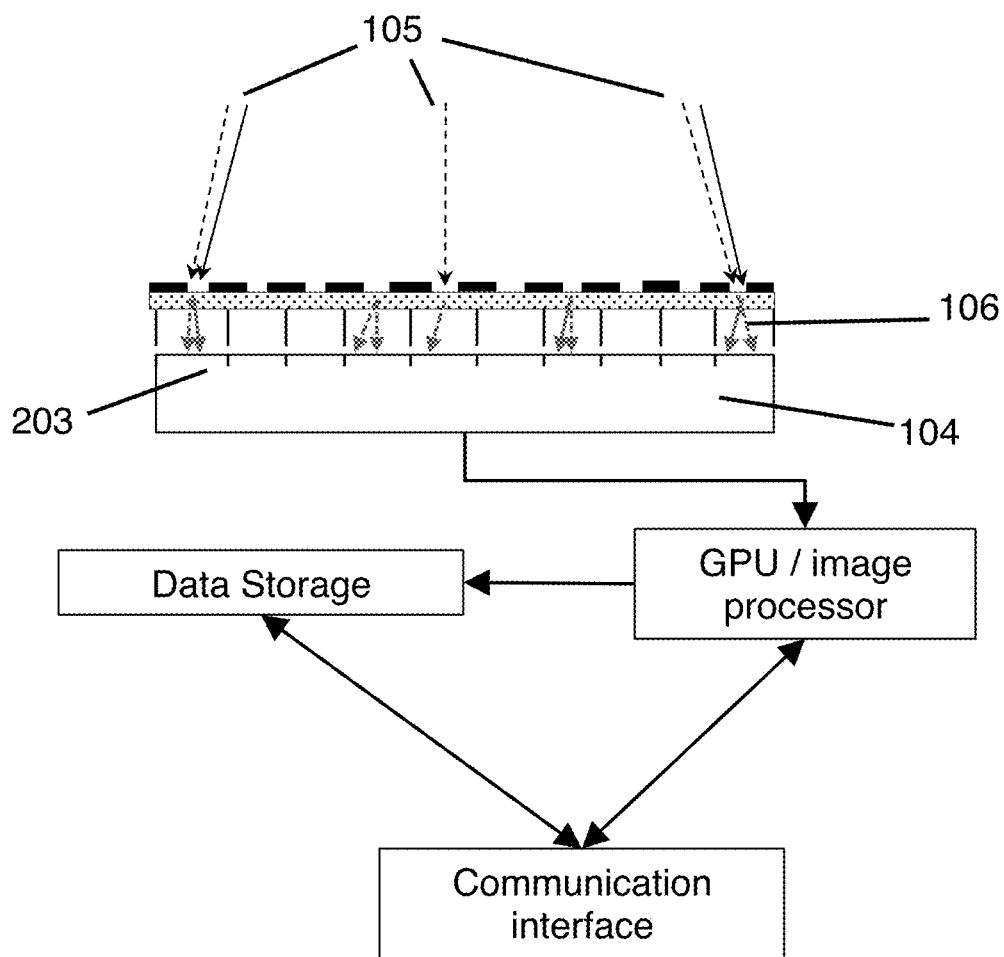
FIG. 14 shows an exemplary data processing scheme useful with embodiments of mapping spectrometers for real-time processing of speckle pattern data.

FIG. 14 shows an exemplary data processing scheme useful with embodiments of mapping spectrometers for real-time processing of speckle pattern data. This scheme may be employed when immediate acquisition of hyperspectral data is required, for example with a manufacturing process for identifying defective products through analyses of spectral signatures in real time. Spectral components 106 of radiation 105 produce speckle patterns on scene elements 203 of detector array 104. The measurement of the speckle patterns by detector array 104 produce data corresponding to the speckle patterns. The speckle pattern data may be immediately processed, with a GPU/image processor for example, or processed in parallel with data acquisition and storage to provide spatial and spectral component information as quickly as possible to a monitor or a system. A communication interface may access spectral, polarization, and spatial data from the GPU/image processor or from the data storage system for offline processing.

Figure 15:
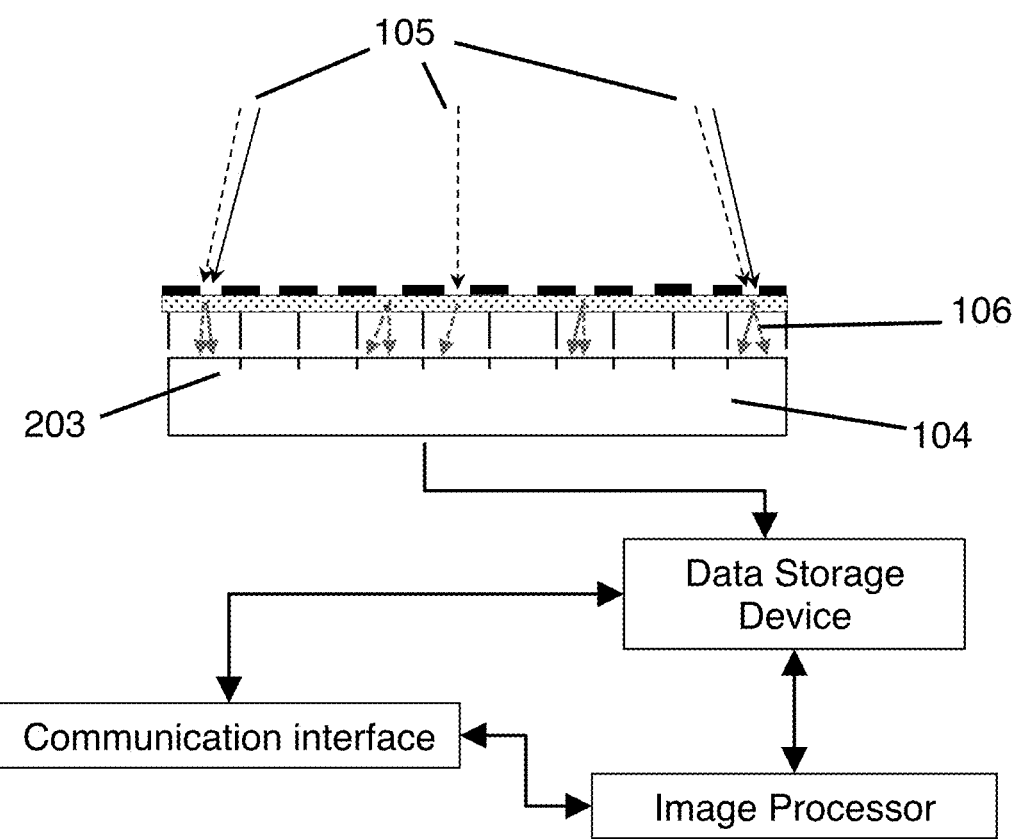
FIG. 15 demonstrates an exemplary data processing scheme useful when immediate data processing is not required.

FIG. 15 demonstrates an exemplary data processing scheme useful when immediate data processing is not required. In this example, data may be processed on demand, at a later time. For example, analysis of spectral, polarization, and spatial information acquired during an aerial survey of crops or when imaging a planetary surface may not have time-critical processing requirements. Spectral components 106 of radiation 105 produce speckle patterns on scene elements 203 of detector array 104. Speckle pattern data resulting from detector array 104 measurements are transferred to a data storage device. An image processor may be in communication with the data storage device to provide determination of spatial, polarization, and spectral component information from data from the storage medium. Processed data having spectral, polarization, and spatial information may be transferred elsewhere via a communication interface or returned to the data storage device for later transfer via the communication interface. This scheme is useful with systems having minimal power availability and/or minimal speed requirements.

Figure 16:
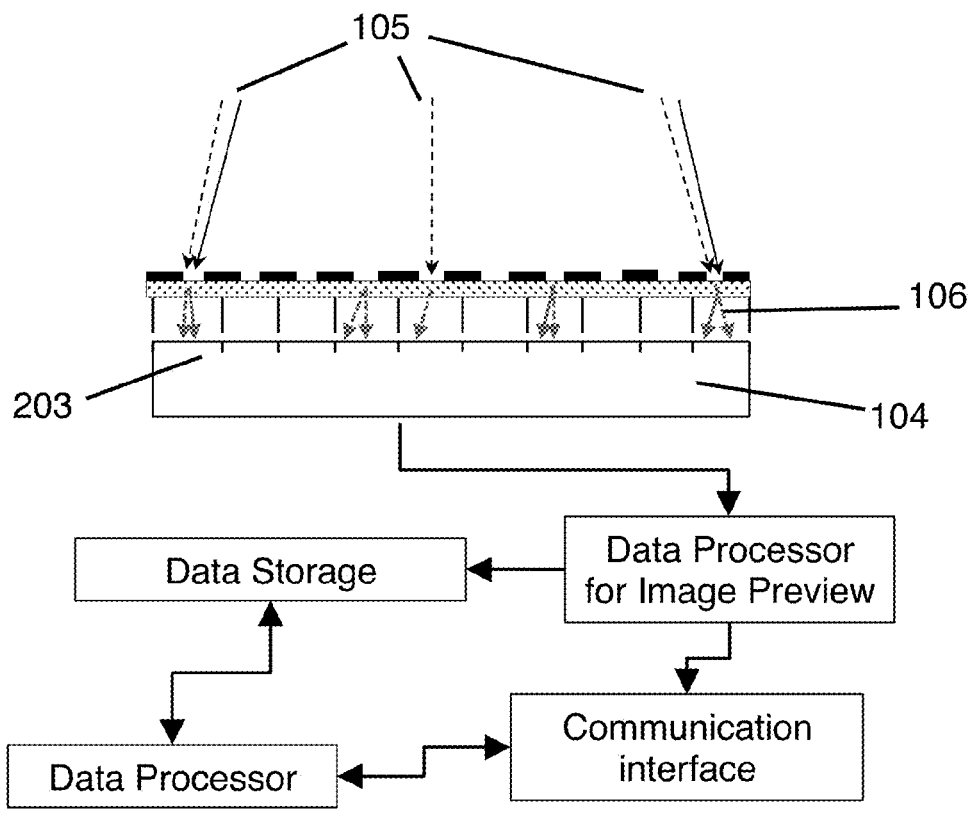
FIG. 16 shows an exemplary data processing scheme useful for providing a real-time image preview when power may be limited.

FIG. 16 shows an exemplary data processing scheme useful for providing a real-time image preview when power may be limited. Such a scheme may be useful, for example, with an aerial surveillance system for providing a rapid preview of spectral, polarization, and spatial data, while also allowing for analysis of the full complement of data on demand at a later time. In this example, a data processor may provide a preview of a scene, such as a panchromatic image or a subset of scene elements. When immediate data processing is not required, data may be processed on demand, at a later time. Spectral components 106 of radiation 105 produce speckle patterns on scene elements 203 of detector array 104. Speckle pattern data from measurements made by the detector array 104 are transferred to a first data processor for a preview of an image. The image preview data processor may be in communication with the data storage device to enable transfer of data from the storage medium for processing. Processed data having spectral, polarization, and spatial information may be transferred elsewhere via a communication interface. This scheme is useful with systems having moderate power availability and minimal speed requirements.

Certain embodiments of the invention are useful for identifying materials. For instance, absorption, florescence, and reflection spectra can reveal electronic or vibrational transitions in a material. Materials excited by lasers can exhibit Raman emission modes that reveal chemically-unique spectroscopic signatures, and the reflectance spectra from surfaces can reveal their composition and/or microstructure. By comparing the computed spectra in a scene element 203 with spectra from a spectroscopy database or a spectral model, it is possible to identify chemical, mineral, and biological elements. Techniques useful for comparing spectra include matched filters and correlation analysis. Furthermore, the use of spatial sensitivity and spatial mapping can provide additional information that can be exploited for the identification of structures. By way of example only, camouflaging may affect perception or appearance of a structure or scene such that it visually appears to be identical to a different structure or scene of an environment. However, when embodiments of the invention are used to determine the spectral signature of the camouflaged structure or region, the signature is unique and identifiable as being different from the item or region it was intended to resemble or mimic. Furthermore, the spatial extent of the camouflage can be determined from the spectral map. In another exemplary embodiment a pair of hyperspectral images may be used to form a spectrally-resolved disparity map, which increases the accuracy of passive computer stereo vision relative to intensity disparity maps.

It is specifically contemplated that embodiments of mapping spectrometers of the invention may comprise the elements described herein in various different combinations and numbers. For example, one spectrometer may comprise any number of a variety of types or sizes of apertures, concentrators, scatterers, and the like. Not all the element or types of elements in various spectrometer embodiments need be the same or have the same characteristics or parameters. By way of example only, it is contemplated that a single spectrometer embodiment may comprise an aperture array that comprises a plurality of different diameters of apertures. By way of a second example, it is contemplated that a single spectrometer embodiment may comprise an aperture array and an array of concentrators that concentrates radiation to less than all apertures in the aperture array. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

All references cited herein are incorporated by reference in their entirety. To the extent publications and patents or patent applications incorporated by reference contradict the invention contained in the specification, the specification will supersede any contradictory material.

What is claimed is:

1. A mapping spectrometer comprising:
a. an array comprising a plurality of apertures and configured to allow for passage of electromagnetic radiation through the apertures;
b. a detector array; and
c. a scatter layer comprising disordered media and positioned to receive electromagnetic radiation passing through the aperture array, wherein the disordered media are selected for scattering spectral components of the received electromagnetic radiation and to direct at least one spectral component of the electromagnetic radiation scattered by the disordered media to the detector array for detection.

2. The spectrometer of claim 1 wherein the array of apertures comprises apertures having diameters that are from about one-tenth times the length of the shortest wavelength of the at least one spectral component to be detected to about one-hundred times the length of the longest wavelength of the at least one spectral component to be detected.

3. The spectrometer of claim 2 wherein the array of apertures comprises apertures having diameters that are from about one-tenth times the length of the shortest wavelength of the at least one spectral component to be detected to about ten times the length of the longest wavelength of the at least one spectral component to be detected.

4. The spectrometer of claim 3 wherein the array of apertures comprises apertures having diameters that are from one-half times the length of the shortest wavelength of the at least one spectral component to be detected to about to two times the length of the longest wavelength of the at least one spectral component to be detected.

5. The spectrometer of claim 1 wherein the diameters of at least two apertures are different from one another.

6. The spectrometer of claim 1 wherein the array of apertures comprises a non-transparent layer comprising perforations.

7. The spectrometer of claim 1 further comprising an aperture array support.

8. The spectrometer of claim 1 further comprising an array comprising a plurality of concentrators configured to concentrate electromagnetic radiation prior to passage of the electromagnetic radiation through the apertures, and wherein each concentrator in the array concentrates radiation to a single aperture of the array of apertures.

9. The spectrometer of claim 8, wherein at least one concentrator comprises an integrated aperture.

10. The spectrometer of claim 8, wherein at least one concentrator comprises a metallic or dielectric coating.

11. The spectrometer of claim 9, wherein at least one concentrator further comprises a tapered transparent medium having a reflective inner surface.

12. The spectrometer of claim 8, wherein at least one concentrator of the concentrator array comprises a first end distal to the aperture array and having a rectangular cross section and a second end proximal to the aperture array and having an elliptical cross section.

13. The spectrometer of claim 1, wherein the scatter layer thickness is from 1 nm to 1 cm inclusive.

14. The spectrometer of claim 1, wherein the distance between the aperture array and the detector array is from 1 nm to 1 cm inclusive.

15. The spectrometer of claim 1, wherein the scatter layer further comprises a transparent medium, and wherein the disordered media are present within or on the transparent scatter layer medium.

16. The spectrometer of claim 15 wherein the transparent scatter layer medium comprises one or more than one of a polymer, glass, or crystal, and wherein the disordered media comprise one or more than one of ceramic particles or polymer particles.

17. The spectrometer of claim 16 wherein the transparent scatter layer medium comprises a polymer.

18. The spectrometer of claim 1, wherein the disordered media comprise a metal film having a thickness from 5 nm to 5,000 nm.

19. The spectrometer of claim 1, wherein the disordered media comprise an agglomeration of metal, ceramic, or polymer particles.

20. The spectrometer of claim 15, wherein the disordered media comprise an agglomeration of metal, ceramic, or polymer particles.

21. The spectrometer of claim 17 wherein the disordered media further comprise an agglomeration of ceramic or polymer particles.

22. The spectrometer of claim 1 further comprising at least one scene element isolator.

23. The spectrometer of 22 wherein the at least one scene element isolator comprises a reflective surface.

24. The spectrometer of claim 1 further comprising imaging optics.

25. The spectrometer of claim 1 further comprising a polarization filter configured to select for polarized electromagnetic radiation prior to passage of the electromagnetic radiation through the array of apertures.

26. The spectrometer of claim 1 further comprising a depolarizing filter configured to randomize the polarization of electromagnetic radiation prior to passage of the electromagnetic radiation through the array of apertures.

27. A camera comprising the mapping spectrometer of claim 1.

28. The spectrometer of claim 1 further comprising a substrate onto which the spectrometer is affixed.

29. The spectrometer of claim 28 wherein the substrate comprises an integrated circuit.

30. A method for analyzing one or more than one spectral components of electromagnetic radiation with a mapping spectrometer of claim 1 comprising:
   a. receiving electromagnetic radiation through the array of apertures to the scatter layer, through the scatter layer, and thence to the detector array;
   b. acquiring data from a speckle pattern produced on the detector array by the at least one scattered spectral component of the received electromagnetic radiation; and,
   c. computationally identifying the at least one scattered spectral component of the electromagnetic radiation scattered by the disordered media, based on the acquired speckle pattern data.

31. A method for analyzing one or more than one spectral components of electromagnetic radiation comprising:
   a. receiving electromagnetic radiation through an array of apertures to a scatter layer comprising disordered media, wherein the disordered media are selected for scattering one or more than one spectral components of the received electromagnetic radiation, through the scatter layer, and thence to a detector array;
   b. acquiring data from a speckle pattern produced on the detector array by the one or more than one spectral components of the electromagnetic radiation scattered by the disordered media; and,
   c. computationally identifying the one or more than one spectral components of the scattered electromagnetic radiation based on the speckle pattern data.

32. The method of claim 30 further comprising:
producing a spectral image using the acquired speckle pattern data.

33. The method of claim 30 further comprising concentrating the electromagnetic radiation prior to passage of the radiation through the apertures.

34. The method of claim 30, further comprising calibrating the spectrometer.

35. The method of claim 30 further comprising identifying the polarization state of the at least one identified spectral component of electromagnetic radiation.

36. The method of claim 30 further comprising identifying spatial information about the electromagnetic radiation.

37. The method of claim 30 wherein the step of computationally identifying comprises implementing an algorithm on the speckle pattern data.

38. The method of claim 37 wherein one or more low-resolution spectral components of the electromagnetic radiation are computationally identified prior to one or more high-resolution spectral components of the electromagnetic radiation.

39. The method of claim 37 wherein the algorithm is implemented on a computer.

40. The method of claim 30 further comprising identifying a mineral, a biological, or a chemical species.

* * * * *

UNITED STATES PATENT AND TRADEMARK OFFICE
CERTIFICATE OF CORRECTION

PATENT NO. : 10,254,164 B2
APPLICATION NO. : 15/099085
DATED : April 9, 2019
INVENTOR(S) : Byron G. Zollars, Chris W. Mann and Gabriel Elpers It is certified that error appears in the above-identified patent and that said Letters Patent is hereby corrected as shown below:

On the Title Page

Item [73], "NANOMMICS" should read --NANOHMICS--

In the Specification

Column 24, Line 1, "L>a×($l^*_{min}$*/a)" should read --(L>a×$l^*_{min}$/a)--

Column 24, Line 35, "a=$x_{min}$ / $\lambda_l$" should read --a=$x_{min} \lambda_l$--

Column 26, after Line 45, in Equation 1,
"$C(r, r'; \Delta v) = \langle I_v(r) I_{v+\Delta v}(r') \rangle - \langle I_v(r) \langle I_v(r) \rangle \langle I_{v+\Delta v}(r') \rangle \rangle$" should read
--$C(r, r'; \Delta v) = \langle I_v(r) I_{v+\Delta v}(r') \rangle - \langle I_v(r) \rangle \langle I_{v+\Delta v}(r') \rangle$--

Column 26, Line 63, "index contrast $m=n_{scatter}$ I /$n_{medium}$" should read --index contrast $m=n_{scatter}/n_{medium}$--

Column 27, after Line 49, Equation 5, "$l^*_{trans}=l^*(1-g)$" should read --$l^*_{trans}=l^*/(1-g)$--

Column 33, Lines 54-55, "A response of C(Δλ,x)=−1 indicates" should read --A response of C(Δλ,x)=1 indicates--

Column 36, Lines 47, "basis vectors for A is measured" should read --basis vectors for ∧ is measured--

Signed and Sealed this
Second Day of August, 2022

Katherine Kelly Vidal
*Director of the United States Patent and Trademark Office*